United States Patent [19]
Lampotang et al.

[11] Patent Number: 6,135,105
[45] Date of Patent: Oct. 24, 2000

[54] LUNG CLASSIFICATION SCHEME, A METHOD OF LUNG CLASS IDENTIFICATION AND INSPIRATORY WAVEFORM SHAPES

[75] Inventors: Samsun Lampotang; Johannes Hugo Maria van Oostrom, both of Gainesville, Fla.

[73] Assignee: University of Florida, Gainesville, Fla.

[21] Appl. No.: 08/546,301

[22] Filed: Oct. 20, 1995

[51] Int. Cl.[7] .................................................. A61M 16/00
[52] U.S. Cl. .................. 128/204.21; 128/204.18
[58] Field of Search ........... 128/204.18, 204.21–204.23, 128/204.26

[56] References Cited

U.S. PATENT DOCUMENTS

| | | | |
|---|---|---|---|
| 3,523,529 | 8/1970 | Kissen | 128/2.07 |
| 3,695,254 | 10/1972 | Blum | 128/2.08 |
| 3,713,436 | 1/1973 | Hardway, Jr. | 128/2.08 |
| 3,961,627 | 6/1976 | Ernst et al. | 128/204.23 |
| 4,031,885 | 6/1977 | Davis et al. | 128/2.08 |
| 4,036,221 | 7/1977 | Hillsman et al. | 128/204.23 |
| 4,351,344 | 9/1982 | Stenzler | 128/720 |
| 4,440,177 | 4/1984 | Anderson et al. | 128/719 |
| 4,796,639 | 1/1989 | Snow et al. | 128/719 |
| 5,003,985 | 4/1991 | White et al. | 128/716 |
| 5,261,397 | 11/1993 | Grunstein | 128/204.18 |

*Primary Examiner*—Aaron J. Lewis
*Attorney, Agent, or Firm*—Needle & Rosenberg, P.C.

[57] ABSTRACT

A method of ventilating a patient comprises initially determining the class of the lungs of a given patient, selecting a pressure or flowrate inspiratory waveform and other ventilatory parameters like inspiratory pause and inspiratory time, among others, appropriate for that lung class, and then ventilating the patient with the selected inspiratory waveform and other ventilatory parameters. New ventilation inspiratory waveforms are provided which have been found to be advantageous for certain lung classes.

31 Claims, 16 Drawing Sheets

| | Ventilation Parameters | | | | Before Pause | | End of Inspiration | | | | | |
|---|---|---|---|---|---|---|---|---|---|---|---|---|
| mode | shape | $T_i$ (s) | VT (l) | pause (% $T_i$) | $V_t/V_I$ | MLP (cm $H_2O$) | $R_s(T_i)$ $V_t/V_I$ | MLP (cm $H_2O$) | PIP (cm $H_2O$) | $Q_{max}$ (l/min) | system τ (s) | Iter. |
| flow | const | 2.0 | 0.7 | 0 | - | - | 1.000 | 7.00 | 15.04 | 21.0 | - | - |
| flow | const | 4.0 | 0.7 | 0 | - | - | 1.000 | 7.00 | 14.52 | 10.5 | - | - |
| flow | const | 2.0 | 1.0 | 0 | - | - | 1.000 | 10.01 | 21.49 | 30.0 | - | - |
| flow | const | 2.0 | 0.7 | 25 | 1.000 | 7.00 | 1.000 | 8.75 | 15.39 | 28.0 | - | - |
| flow | inc. | 2.0 | 0.7 | 0 | - | - | 1.000 | 4.67 | 16.09 | 42.0 | - | - |
| flow | dec. | 2.0 | 0.7 | 0 | - | - | 1.000 | 9.34 | 14.08 | 42.0 | - | - |
| flow | h-sin | 2.0 | 0.7 | 0 | - | - | 1.000 | 7.00 | 14.19 | 33.0 | - | - |
| flow | q-sin | 2.0 | 0.7 | 0 | - | - | 1.000 | 8.92 | 14.10 | 33.0 | - | - |
| flow | trap. | 2.0 | 0.7 | 0 | - | - | 1.000 | 8.56 | 14.10 | 28.0 | - | - |
| flow | d_exp | 2.0 | 0.7 | 0 | - | - | 1.000 | 11.31 | 14.05 | 105.7 | - | - |
| flow | sh-sin | 2.0 | 0.7 | 0 | - | - | 1.000 | 10.36 | 14.04 | 57.8 | - | - |
| flow | r_exp | 2.0 | 0.7 | 0 | - | - | 1.000 | 2.71 | 19.22 | 105.4 | - | - |
| press. | const | 2.0 | 0.7 | 0 | - | - | 1.000 | 12.96 | 14.00 | 280.0 | 0.15 | 4 |
| press. | inc. | 2.0 | 0.7 | 0 | - | - | 1.000 | 6.52 | 15.13 | 22.7 | - | 4 |
| press. | r_exp | 2.0 | 0.7 | 0 | - | - | 1.000 | 2.78 | 19.20 | 104.8 | - | 4 |
| flow | inc. | 2.0 | 0.7 | 25 | 1.000 | 4.67 | 1.000 | 7.00 | 16.78 | 56.0 | - | - |
| flow | dec. | 2.0 | 0.7 | 25 | 1.000 | 9.34 | 1.000 | 10.50 | 14.14 | 56.0 | - | - |
| flow | h-sin | 2.0 | 0.7 | 25 | 1.000 | 7.00 | 1.000 | 8.75 | 14.34 | 44.0 | - | - |
| flow | q-sin | 2.0 | 0.7 | 25 | 1.000 | 8.92 | 1.000 | 10.19 | 14.18 | 44.0 | - | - |
| flow | trap. | 2.0 | 0.7 | 25 | 1.000 | 8.56 | 1.000 | 9.92 | 14.17 | 37.3 | - | - |
| flow | d_exp | 2.0 | 0.7 | 25 | 1.000 | 11.32 | 1.000 | 12.00 | 14.07 | 141.0 | - | - |
| flow | sh-sin | 2.0 | 0.7 | 25 | 1.000 | 10.36 | 1.000 | 11.28 | 14.08 | 77.1 | - | - |
| flow | r_exp | 2.0 | 0.7 | 25 | 1.000 | 2.71 | 1.000 | 5.52 | 20.95 | 140.5 | - | - |
| press. | const | 2.0 | 0.7 | 25 | 1.000 | 12.61 | 1.000 | 12.96 | 14.00 | 280.0 | 0.15 | 4 |
| press. | inc. | 2.0 | 0.7 | 25 | 1.000 | 6.38 | 1.000 | 8.29 | 15.54 | 31.1 | - | 3 |
| press. | r_exp | 2.0 | 0.7 | 25 | 1.000 | 2.78 | 1.000 | 5.58 | 20.94 | 139.8 | - | 4 |

Fig. 5

| | Ventilation Parameters | | | | Before Pause | | End of Inspiration | | | | | |
|---|---|---|---|---|---|---|---|---|---|---|---|---|
| mode | shape | $T_i$ (s) | VT (l) | pause (% $T_i$) | $V_t/V_i$ | MLP (cm $H_2O$) | $R_s(T_i)$ $V_t/V_i$ | MLP (cm $H_2O$) | PIP (cm $H_2O$) | $Q_{max}$ (l/min) | system τ (s) | Iter. |
| flow | const | 2.0 | 0.7 | 0 | - | - | 0.519 | 9.45 | 19.82 | 21.0 | - | - |
| flow | const | 4.0 | 0.7 | 0 | - | - | 0.509 | 9.39 | 19.25 | 10.5 | - | - |
| flow | const | 2.0 | 1.0 | 0 | - | - | 0.519 | 13.50 | 28.32 | 30.0 | - | - |
| flow | const | 2.0 | 0.7 | 25 | 0.525 | 9.49 | 0.500 | 11.79 | 20.21 | 28.0 | - | - |
| flow | inc. | 2.0 | 0.7 | 0 | - | - | 0.537 | 6.33 | 20.97 | 42.0 | - | - |
| flow | dec. | 2.0 | 0.7 | 0 | - | - | 0.502 | 12.57 | 18.75 | 42.0 | - | - |
| flow | h-sin | 2.0 | 0.7 | 0 | - | - | 0.505 | 9.45 | 18.87 | 33.0 | - | - |
| flow | q-sin | 2.0 | 0.7 | 0 | - | - | 0.502 | 12.01 | 18.78 | 33.0 | - | - |
| flow | trap. | 2.0 | 0.7 | 0 | - | - | 0.502 | 11.53 | 18.77 | 28.0 | - | - |
| flow | d_exp | 2.0 | 0.7 | 0 | - | - | 0.501 | 15.20 | 18.73 | 105.7 | - | - |
| flow | sh-sin | 2.0 | 0.7 | 0 | - | - | 0.500 | 13.93 | 18.71 | 57.8 | - | - |
| flow | r_exp | 2.0 | 0.7 | 0 | - | - | 0.580 | 3.70 | 24.34 | 105.4 | - | - |
| press. | const | 2.0 | 0.7 | 0 | - | - | 0.500 | 17.63 | 18.67 | 373.3 | 0.106 | 4 |
| press. | inc. | 2.0 | 0.7 | 0 | - | - | 0.520 | 8.91 | 19.89 | 22.4 | - | 3 |
| press. | r_exp | 2.0 | 0.7 | 0 | - | - | 0.579 | 3.80 | 24.32 | 104.8 | - | 4 |
| flow | inc. | 2.0 | 0.7 | 25 | 0.548 | 6.37 | 0.500 | 9.46 | 21.73 | 56.0 | - | - |
| flow | dec. | 2.0 | 0.7 | 25 | 0.503 | 12.61 | 0.500 | 14.12 | 18.82 | 56.0 | - | - |
| flow | h-sin | 2.0 | 0.7 | 25 | 0.508 | 9.47 | 0.500 | 11.78 | 19.02 | 44.0 | - | - |
| flow | q-sin | 2.0 | 0.7 | 25 | 0.504 | 12.05 | 0.500 | 13.71 | 18.86 | 44.0 | - | - |
| flow | trap. | 2.0 | 0.7 | 25 | 0.504 | 11.56 | 0.500 | 13.34 | 18.85 | 37.3 | - | - |
| flow | d_exp | 2.0 | 0.7 | 25 | 0.501 | 15.25 | 0.500 | 16.11 | 18.75 | 141.0 | - | - |
| flow | sh-sin | 2.0 | 0.7 | 25 | 0.501 | 13.97 | 0.500 | 15.15 | 18.75 | 77.1 | - | - |
| flow | r_exp | 2.0 | 0.7 | 25 | 0.601 | 3.72 | 0.501 | 7.48 | 26.18 | 140.5 | - | - |
| press. | const | 2.0 | 0.7 | 25 | 0.500 | 17.27 | 0.500 | 17.61 | 18.65 | 373 | 0.106 | 3 |
| press. | inc. | 2.0 | 0.7 | 25 | 0.528 | 8.79 | 0.500 | 11.27 | 20.35 | 30.5 | - | 3 |
| press. | r_exp | 2.0 | 0.7 | 25 | 0.600 | 3.82 | 0.501 | 7.56 | 26.17 | 139.8 | - | 4 |

Fig. 6

| | Ventilation Parameters | | | | Before Pause | | End of Inspiration | | | | | |
|---|---|---|---|---|---|---|---|---|---|---|---|---|
| mode | shape | $T_i$ (s) | VT (l) | pause (% $T_i$) | $V_t/V_i$ | MLP (cm $H_2O$) | $R_s(T_i)$ $V_t/V_i$ | MLP (cm $H_2O$) | PIP (cm $H_2O$) | $Q_{max}$ (l/min) | system $\tau$ (s) | Iter. |
| flow | const | 2.0 | 0.7 | 0 | - | - | 1.078 | 7.00 | 15.57 | 21.0 | - | - |
| flow | const | 4.0 | 0.7 | 0 | - | - | 1.038 | 7.00 | 14.78 | 10.5 | - | - |
| flow | const | 2.0 | 1.0 | 0 | - | - | 1.078 | 10.01 | 22.24 | 30.0 | - | - |
| flow | const | 2.0 | 0.7 | 25 | 1.105 | 7.01 | 1.011 | 8.75 | 16.09 | 28.0 | - | - |
| flow | inc. | 2.0 | 0.7 | 0 | - | - | 1.143 | 4.67 | 17.10 | 42.0 | - | - |
| flow | dec. | 2.0 | 0.7 | 0 | - | - | 1.017 | 9.34 | 14.22 | 42.0 | - | - |
| flow | h-sin | 2.0 | 0.7 | 0 | - | - | 1.038 | 7.00 | 14.49 | 33.0 | - | - |
| flow | q-sin | 2.0 | 0.7 | 0 | - | - | 1.020 | 8.92 | 14.27 | 33.0 | - | - |
| flow | trap. | 2.0 | 0.7 | 0 | - | - | 1.022 | 8.56 | 14.28 | 28.0 | - | - |
| flow | d_exp | 2.0 | 0.7 | 0 | - | - | 1.006 | 11.31 | 14.08 | 105.7 | - | - |
| flow | sh-sin | 2.0 | 0.7 | 0 | - | - | 1.006 | 10.36 | 14.14 | 57.8 | - | - |
| flow | r_exp | 2.0 | 0.7 | 0 | - | - | 1.275 | 2.71 | 21.54 | 105.5 | - | - |
| press. | const | 2.0 | 0.7 | 0 | - | - | 1.001 | 12.43 | 14.00 | 210.0 | 0.188 | 4 |
| press. | inc. | 2.0 | 0.7 | 0 | - | - | 1.088 | 6.34 | 15.76 | 23.6 | - | 4 |
| press. | r_exp | 2.0 | 0.7 | 0 | - | - | 1.273 | 2.77 | 21.51 | 104.9 | - | 4 |
| flow | inc. | 2.0 | 0.7 | 25 | 1.186 | 4.67 | 1.019 | 7.00 | 18.11 | 56.0 | - | - |
| flow | dec. | 2.0 | 0.7 | 25 | 1.030 | 9.34 | 1.003 | 10.50 | 14.38 | 56.0 | - | - |
| flow | h-sin | 2.0 | 0.7 | 25 | 1.063 | 7.00 | 1.007 | 8.75 | 14.84 | 44.0 | - | - |
| flow | q-sin | 2.0 | 0.7 | 25 | 1.035 | 8.92 | 1.004 | 10.19 | 14.46 | 44.0 | - | - |
| flow | trap. | 2.0 | 0.7 | 25 | 1.039 | 8.56 | 1.004 | 9.92 | 14.49 | 37.3 | - | - |
| flow | exp. | 2.0 | 0.7 | 25 | 1.011 | 11.32 | 1.001 | 12.0 | 14.11 | 141.0 | - | - |
| flow | sh-sin | 2.0 | 0.7 | 25 | 1.014 | 10.36 | 1.002 | 11.28 | 14.31 | 77.1 | - | - |
| flow | r_exp | 2.0 | 0.7 | 25 | 1.336 | 2.71 | 1.032 | 5.52 | 23.96 | 140.5 | - | - |
| press. | const | 2.0 | 0.7 | 25 | 1.007 | 11.96 | 1.001 | 12.47 | 14.05 | 210.7 | 0.188 | 4 |
| press. | inc. | 2.0 | 0.7 | 25 | 1.123 | 6.18 | 1.013 | 8.13 | 16.44 | 32.8 | - | 3 |
| press. | r_exp | 2.0 | 0.7 | 25 | 1.334 | 2.77 | 1.031 | 5.58 | 23.93 | 139.7 | - | 3 |

Fig. 7

| | Ventilation Parameters | | | | Before Pause | | End of Inspiration | | | | | |
|---|---|---|---|---|---|---|---|---|---|---|---|---|
| mode | shape | T$_i$ (s) | VT (l) | pause (% T$_i$) | V$_r$/V$_i$ | MLP (cm H$_2$O) | R$_r$(T$_i$) V$_r$/V$_i$ | MLP (cm H$_2$O) | PIP (cm H$_2$O) | Q$_{max}$ (l/min) | system τ (s) | Iter. |
| flow | const | 2.0 | 0.7 | 0 | - | - | 0.558 | 9.66 | 20.76 | 21.0 | - | - |
| flow | const | 4.0 | 0.7 | 0 | - | - | 0.529 | 9.50 | 19.71 | 10.5 | - | - |
| flow | const | 2.0 | 1.0 | 0 | - | - | 0.558 | 13.80 | 29.65 | 30.0 | - | - |
| flow | const | 2.0 | 0.7 | 25 | 0.579 | 9.76 | 0.503 | 12.02 | 21.45 | 28.0 | - | - |
| flow | inc. | 2.0 | 0.7 | 0 | - | - | 0.612 | 6.53 | 22.74 | 42.0 | - | - |
| flow | dec. | 2.0 | 0.7 | 0 | - | - | 0.508 | 12.80 | 19.01 | 42.0 | - | - |
| flow | h-sin | 2.0 | 0.7 | 0 | - | - | 0.520 | 9.67 | 19.44 | 33.0 | - | - |
| flow | q-sin | 2.0 | 0.7 | 0 | - | - | 0.510 | 12.24 | 19.09 | 33.0 | - | - |
| flow | trap. | 2.0 | 0.7 | 0 | - | - | 0.511 | 11.75 | 19.11 | 28.0 | - | - |
| flow | d_exp | 2.0 | 0.7 | 0 | - | - | 0.503 | 15.43 | 18.78 | 105.7 | - | - |
| flow | sh-sin | 2.0 | 0.7 | 0 | - | - | 0.502 | 14.16 | 18.90 | 57.8 | - | - |
| flow | r_exp | 2.0 | 0.7 | 0 | - | - | 0.739 | 3.86 | 28.18 | 105.5 | - | - |
| press. | const | 2.0 | 0.7 | 0 | - | - | 0.501 | 16.94 | 18.68 | 280.2 | 0.116 | 4 |
| press. | inc. | 2.0 | 0.7 | 0 | - | - | 0.566 | 8.80 | 21.01 | 23.6 | - | 3 |
| press. | r_exp | 2.0 | 0.7 | 0 | - | - | 0.737 | 3.96 | 28.22 | 104.9 | - | 4 |
| flow | inc. | 2.0 | 0.7 | 25 | 0.648 | 6.61 | 0.505 | 9.69 | 24.05 | 56.0 | - | - |
| flow | dec. | 2.0 | 0.7 | 25 | 0.515 | 12.91 | 0.501 | 14.35 | 19.27 | 56.0 | - | - |
| flow | h-sin | 2.0 | 0.7 | 25 | 0.534 | 9.78 | 0.501 | 12.02 | 19.98 | 44.0 | - | - |
| flow | q-sin | 2.0 | 0.7 | 25 | 0.518 | 12.35 | 0.501 | 13.94 | 19.40 | 44.0 | - | - |
| flow | trap. | 2.0 | 0.7 | 25 | 0.520 | 11.86 | 0.501 | 13.57 | 19.45 | 37.3 | - | - |
| flow | d_exp | 2.0 | 0.7 | 25 | 0.505 | 15.56 | 0.500 | 16.34 | 18.82 | 141.0 | - | - |
| flow | sh-sin | 2.0 | 0.7 | 25 | 0.505 | 14.28 | 0.500 | 14.28 | 19.19 | 77.1 | - | - |
| flow | r_exp | 2.0 | 0.7 | 25 | 0.803 | 3.92 | 0.509 | 7.71 | 31.06 | 140.5 | - | - |
| press. | const | 2.0 | 0.7 | 25 | 0.503 | 16.43 | 0.500 | 16.99 | 18.75 | 281.3 | 0.116 | 4 |
| press. | inc. | 2.0 | 0.7 | 25 | 0.593 | 8.70 | 0.503 | 11.23 | 21.92 | 32.7 | - | 3 |
| press. | r_exp | 2.0 | 0.7 | 25 | 0.800 | 4.01 | 0.509 | 7.79 | 31.03 | 139.8 | - | 3 |

Fig. 8

| | Ventilation Parameters | | | | Before Pause | | End of Inspiration | | | | | |
|---|---|---|---|---|---|---|---|---|---|---|---|---|
| mode | shape | $T_i$ (s) | VT (l) | pause (% $T_i$) | $V_r/V_i$ | MLP (cm $H_2O$) | $R_r(T_i)$ $V_r/V_i$ | MLP (cm $H_2O$) | PIP (cm $H_2O$) | $Q_{max}$ (l/min) | system $\tau$ (s) | iter. |
| flow | const | 2.0 | 0.7 | 0 | - | - | 2.891 | 7.12 | 15.44 | *21.0* | - | - |
| flow | const | *4.0* | 0.7 | 0 | - | - | 2.945 | 7.07 | 14.72 | 10.5 | - | - |
| flow | const | 2.0 | *1.0* | 0 | - | - | 2.891 | 10.18 | 22.05 | 30.0 | - | - |
| flow | const | 2.0 | 0.7 | *25* | 2.855 | 7.16 | 2.992 | 8.88 | 15.92 | 28.0 | - | - |
| flow | inc. | 2.0 | 0.7 | 0 | - | - | 2.804 | 4.78 | 16.87 | 42.0 | - | - |
| flow | dec. | 2.0 | 0.7 | 0 | - | - | 2.981 | 9.47 | 14.16 | 42.0 | - | - |
| flow | h-sin | 2.0 | 0.7 | 0 | - | - | 2.957 | 7.13 | 14.37 | 33.0 | - | - |
| flow | q-sin | 2.0 | 0.7 | 0 | - | - | 2.977 | 9.05 | 14.20 | 33.0 | - | - |
| flow | trap. | 2.0 | 0.7 | 0 | - | - | 2.975 | 8.69 | 14.20 | 28.0 | - | - |
| flow | d_exp | 2.0 | 0.7 | 0 | - | - | 2.993 | 11.44 | 14.07 | 105.7 | - | - |
| flow | sh-sin | 2.0 | 0.7 | 0 | - | - | 2.995 | 10.49 | 14.09 | 57.8 | - | - |
| flow | r_exp | 2.0 | 0.7 | 0 | - | - | *2.637* | *2.80* | *21.13* | 105.5 | - | - |
| press. | const | 2.0 | 0.7 | 0 | - | - | *3.000* | *12.69* | *14.00* | 209.9 | 0.197 | 4 |
| press. | inc. | 2.0 | 0.7 | 0 | - | - | 2.878 | 6.49 | 15.60 | 23.4 | - | 4 |
| press. | r_exp | 2.0 | 0.7 | 0 | - | - | 2.640 | 2.87 | 21.10 | 104.8 | - | 4 |
| flow | inc. | 2.0 | 0.7 | 25 | 2.750 | 4.81 | 2.986 | 7.13 | 17.82 | 56.0 | - | - |
| flow | dec. | 2.0 | 0.7 | 25 | 2.967 | 9.51 | 2.998 | 10.64 | 14.28 | 56.0 | - | - |
| flow | h-sin | 2.0 | 0.7 | 25 | 2.927 | 7.17 | 2.996 | 8.88 | 14.65 | 44.0 | - | - |
| flow | q-sin | 2.0 | 0.7 | 25 | 2.960 | 9.09 | 2.998 | 10.32 | 14.34 | 44.0 | - | - |
| flow | trap. | 2.0 | 0.7 | 25 | 2.956 | 8.73 | 2.998 | 10.05 | 14.36 | 37.3 | - | - |
| flow | d_exp | 2.0 | 0.7 | 25 | 2.989 | 11.49 | 3.000 | 12.13 | 14.09 | 141.0 | - | - |
| flow | sh-sin | 2.0 | 0.7 | 25 | 2.988 | 10.54 | 3.000 | 11.41 | 14.19 | 77.1 | - | - |
| flow | r_exp | 2.0 | 0.7 | 25 | 2.568 | 2.82 | 2.975 | 5.65 | 23.48 | 140.5 | - | - |
| press. | const | 2.0 | 0.7 | 25 | 2.996 | 12.27 | 3.000 | 12.70 | 14.01 | 210.2 | 0.197 | 4 |
| press. | inc. | 2.0 | 0.7 | 25 | 2.834 | 6.35 | 2.991 | 8.28 | 16.21 | 32.4 | - | 3 |
| press. | r_exp | 2.0 | 0.7 | 25 | 2.571 | 2.88 | 2.976 | 5.71 | 23.45 | 139.7 | - | 3 |

Fig. 9

| Ventilation Parameters | | | | | Before Pause | | End of Inspiration | | | | | |
|---|---|---|---|---|---|---|---|---|---|---|---|---|
| mode | shape | $T_i$ (s) | VT (l) | pause (% $T_i$) | $V_r/V_t$ | MLP (cm $H_2O$) | $R_r(T_i)$ $V_r/V_t$ | MLP (cm $H_2O$) | PIP (cm $H_2O$) | $Q_{max}$ (l/min) | system $\tau$ (s) | Iter. |
| flow | const | 2.0 | 0.7 | 0 | - | - | 2.000 | 9.34 | 20.06 | 21.0 | - | - |
| flow | const | 4.0 | 0.7 | 0 | - | - | 2.000 | 9.34 | 19.36 | 10.5 | - | - |
| flow | const | 2.0 | 1.0 | 0 | - | - | 2.000 | 13.34 | 28.65 | 30.0 | - | - |
| flow | const | 2.0 | 0.7 | 25 | 2.000 | 9.34 | 2.000 | 11.67 | 20.52 | 28.0 | - | - |
| flow | inc. | 2.0 | 0.7 | 0 | - | - | 2.000 | 6.23 | 21.45 | 42.0 | - | - |
| flow | dec. | 2.0 | 0.7 | 0 | - | - | 2.000 | 12.44 | 18.77 | 42.0 | - | - |
| flow | h-sin | 2.0 | 0.7 | 0 | - | - | 2.000 | 9.33 | 18.92 | 33.0 | - | - |
| flow | q-sin | 2.0 | 0.7 | 0 | - | - | 2.000 | 11.89 | 18.80 | 33.0 | - | - |
| flow | trap. | 2.0 | 0.7 | 0 | - | - | 2.000 | 11.41 | 18.79 | 28.0 | - | - |
| flow | d_exp | 2.0 | 0.7 | 0 | - | - | 2.000 | 15.08 | 18.74 | 105.7 | - | - |
| flow | sh-sin | 2.0 | 0.7 | 0 | - | - | 2.000 | 13.81 | 18.71 | 57.8 | - | - |
| flow | r_exp | 2.0 | 0.7 | 0 | - | - | 2.000 | 3.61 | 25.63 | 105.5 | - | - |
| press. | const | 2.0 | 0.7 | 0 | - | - | 2.000 | 17.28 | 18.67 | 280.0 | 0.15 | 4 |
| press. | inc. | 2.0 | 0.7 | 0 | - | - | 2.000 | 8.70 | 20.17 | 22.7 | - | 4 |
| press. | r_exp | 2.0 | 0.7 | 0 | - | - | 2.000 | 3.70 | 25.59 | 104.8 | - | 4 |
| flow | inc. | 2.0 | 0.7 | 25 | 2.000 | 6.23 | 2.000 | 9.34 | 22.37 | 56.0 | - | - |
| flow | dec. | 2.0 | 0.7 | 25 | 2.000 | 12.45 | 2.000 | 14.00 | 18.85 | 56.0 | - | - |
| flow | h-sin | 2.0 | 0.7 | 25 | 2.000 | 9.33 | 2.000 | 11.67 | 19.11 | 44.0 | - | - |
| flow | q-sin | 2.0 | 0.7 | 25 | 2.000 | 11.89 | 2.000 | 13.59 | 18.90 | 44.0 | - | - |
| flow | trap. | 2.0 | 0.7 | 25 | 2.000 | 11.41 | 2.000 | 13.22 | 18.90 | 37.3 | - | - |
| flow | d_exp | 2.0 | 0.7 | 25 | 2.000 | 15.09 | 2.000 | 15.99 | 18.76 | 141.0 | - | - |
| flow | sh-sin | 2.0 | 0.7 | 25 | 2.000 | 13.82 | 2.000 | 15.04 | 18.77 | 77.1 | - | - |
| flow | r_exp | 2.0 | 0.7 | 25 | 2.000 | 3.61 | 2.000 | 7.36 | 27.94 | 140.5 | - | - |
| press. | const | 2.0 | 0.7 | 25 | 2.000 | 16.81 | 2.000 | 17.28 | 18.67 | 280.0 | 0.15 | 4 |
| press. | inc. | 2.0 | 0.7 | 25 | 2.000 | 8.51 | 2.000 | 11.05 | 20.72 | 31.1 | - | 3 |
| press. | r_exp | 2.0 | 0.7 | 25 | 2.000 | 3.70 | 2.000 | 7.44 | 27.92 | 139.8 | - | 4 |

Fig. 10

|  | Type 1 $R_r = R_i$ $C_r = C_i$ $\tau_r = \tau_i$ | Type 2 $R_r = R_i$ $C_r \neq C_i$ $\tau_r \neq \tau_i$ | Type 3 $R_r \neq R_i$ $C_r = C_i$ $\tau_r \neq \tau_i$ | Type 4 $R_r < R_i$ $C_r < C_i$ $\tau_r \neq \tau_i$ | Type 5 $R_r < R_i$ $C_r > C_i$ $\tau_r \neq \tau_i$ | Type 5a $R_r < R_i$ $C_r > C_i$ $\tau_r = \tau_i$ |
|---|---|---|---|---|---|---|
| Influence of shape on $R_v$ | none | yes | yes | yes | yes | none |
| Shape *without pause* with $R_v$ closest to 1.0 | all shapes: $R_v = 1.0$ | inc. exp. flow/press. | const press. | inc. exp. flow/press. | inc. exp. flow/press. | all shapes: $R_v = C_r/C_i$ |
| Shape *without pause* with $R_v$ farthest from 1.0 | $R_v = 1.0$ for all shapes | const press. sh-sin flow | inc. exp. flow/press. | const press. sh-sin flow | const press. sh-sin flow | $R_v = C_r/C_i$ for all shapes |
| Shape with lowest mean lung pressure over time | inc. exp. flow/press. | inc. exp. flow/press. | inc. exp. flow/press. | inc. exp. flow/press. | inc. exp. flow/press. | inc. exp. flow/press. |
| Shape with highest mean lung pressure over time | const press. | const press. | const press. | const press. | const press. | const press. |
| Effect of increased $T_i$ on $R_v = V_r/V_i$ | none for all shapes | worse or no improvement for all shapes | improved for all shapes | worse for all shapes | worse for all shapes | none for all shapes |
| Effect of increased $T_i$ on MLP($T_i$) | none for all flow shapes & r_exp, press.; ↑ for other press. shapes | ↓ for all flow shapes and r_exp, press.; ↑ for other press. shapes; | none for all flow shapes & r_exp, press.; ↑ for other press. shapes | ↓ for all flow shapes & r_exp, press; ↑ for other press. shapes | ↓ for all flow shapes & r_exp, press; ↑ for other press. shapes | none for all flow shapes & r_exp, press; ↑ for other press. shapes |
| Effect of inspiratory pause on $R_v$ | none for all shapes | worse or no improvement for all shapes | better for all shapes; const press. unchanged | worse for all shapes | worse for all shapes; const press. unchanged | none for all shapes |
| Effect of inspiratory pause on MLP($T_i$) | ↑ for all shapes; none for const press. | ↑ for all shapes; none for const press. | ↑ for all shapes; none for const press. | ↑ for all shapes; none for const press. | ↑ for all shapes; none for const press. | ↑ for all shapes; none for const press. |
| Effect of increased VT with const flow shape | none on $R_v$ ↑ MLP, ↑ PIP | none on $R_v$ ↑ MLP, ↑ PIP | none on $R_v$ ↑ MLP, ↑ PIP | none on $R_v$ ↑ MLP, ↑ PIP | none on $R_v$ ↑ MLP, ↑ PIP | none on $R_v$ ↑ MLP, ↑ PIP |
| Lowest pressure at carina (PIP) | const press. | const press. | const press. | const press. | const press. | const press. |
| Highest pressure at carina (PIP) | inc. exp. flow/press. | inc. exp. flow/press. | inc. exp. flow/press. | inc. exp. press./flow | inc. exp. flow/press. | inc. exp. flow/press. |

Fig. 11

LUNG CLASSIFICATION SCHEME, A METHOD OF LUNG CLASS IDENTIFICATION AND INSPIRATORY WAVEFORM SHAPES

FIELD OF THE INVENTION

This invention relates to systems for the artificial ventilation of patients, and, more particularly, to a classification scheme for different types of patients' lungs, a method of identifying lung classes, and, a method and apparatus for the delivery of ventilatory parameters including waveform, inspiratory time, inspiratory pause and tidal volume, among others, dependent upon the identified lung class.

BACKGROUND OF THE INVENTION

The lungs can be characterized as a mass exchanger in which oxygen, anesthetics and/or medication are delivered through the alveoli to blood pumped from the heart, and carbon dioxide, and anesthetics during emergence, are removed from the blood for exhalation. The mass transfer rate and efficiency in either direction, i.e. removal or inflow of gaseous materials at the blood/gas interface, is dependent at least in part on the distribution of ventilation to each lung. In turn, mechanical factors such as compliance and flow resistance within the bronchi and the different regions of the lungs affect the distribution of pulmonary ventilation. The term "compliance" refers to the elasticity of the lungs, or their ability to expand and contract during an inspiration and exhalation cycle, and is the inverse or mathematical reciprocal of stiffness. The flow resistance along the respiratory pathways refers to blockages or restrictions to the passage or flow of gaseous materials to and from the lungs.

Diseased or injured lungs may have markedly different compliances or flow resistances compared to healthy lungs. For example, one bronchus may have a higher flow resistance due to swelling of its mucus membrane that constricts its flow area compared to the bronchus associated with the other, unaffected lung. Additionally, one lung could be less compliant than the other due to trauma or aspiration of gastric acid from the stomach. A lung with lower resistance and/or lower compliance builds up pressure at a faster rate than the other lung when both are exposed to a common pressure or flowrate input at the trachea, or at the carina where the bronchi meet the trachea. Consequently, the distribution of ventilation in the lungs can become unequal such that the volume of gas in the right lung at the end of inspiration may not be equal to the volume of gas in the left lung. If both an abnormal lung and a healthy lung receive similar blood perfusion rates (Q), i.e. the same volume of blood from the heart per unit time (cardiac output), but different ventilation or gas volume rates (V), there is an undesirable ventilation/perfusion ratio (V/Q) mismatch. This mismatch degrades the mass transfer or gas exchange rate, and the efficiency of such exchange, within the lungs. In turn, less carbon dioxide (and less gaseous and volatile anesthetics during emergence) come out of solution from the blood, while less oxygen (and less gaseous and volatile anesthetics during induction and maintenance) dissolve into the blood per unit time. Although the body's compensatory mechanisms will shunt the perfusion to favor the better ventilated lung, there is a limit to that self-regulatory action, particularly when it is depressed by some anesthetics.

Another physiological parameter which is of concern during ventilation and/or anesthesia of a patient is the mean pressure within the lungs over time (mean lung pressure, MLP). Higher mean lung pressures during mechanical ventilation can reduce the cardiac output or volume of blood pumped by the heart per unit time by interfering with the filling and emptying of the heart. Because the lungs and heart both reside in the chest cavity, excess pressure, and hence excess expansion of the lungs, can reduce cardiac output.

In view of these problems with ventilation of diseased or injured lungs, one design objective of ventilation apparatus and anesthesia systems is to equalize the distribution of ventilation in lungs of unequal compliances and/or unequal resistances, while minimizing the mean lung pressure within the lungs. We numerically express distribution of ventilation as the "ventilation distribution ratio," or quotient of the volume of gas within the right lung over the volume in the left lung at the end of inspiration. Assuming the right and left lung to be of equal volume, the ventilation distribution ratio ($R_v$) should ideally be unity, or, for diseased or damaged lungs, as close to unity as possible.

A number of studies have been undertaken to determine the effectiveness of inspiratory waveform shaping as a means of optimizing the ventilation distribution ratio of lungs having unequal compliance and/or resistance, while minimizing mean lung pressure. The term "inspiratory waveform shaping" refers to the configuration of a pressure or flowrate waveform over time which is delivered by a ventilator (ICU (intensive care unit) or anesthesia) to the patient during mechanical inspiration. Currently, there are four flowrate waveforms commonly employed in ICU ventilators, including constant flowrate, linearly increasing flowrate, linearly decreasing flowrate and half-sine (0 to $\pi$) flowrate. Most anesthesia ventilators offer only a constant flowrate waveform. These flowrate waveforms have been utilized in various studies to assess the effect of using one waveform or another on the ventilation distribution ratio for different lung configurations, e.g. lungs having equal compliance and unequal resistance (ECUR), and lungs with unequal compliance and equal resistance (UCER).

The results obtained from prior studies involving inspiratory waveform shaping have up to now contradicted one another. Furthermore, none of the studies have addressed the need for a lung classification scheme or how to identify/classify a patient's lung configuration. No suggestion is made as to how one might determine the particular characteristics of the lung of a given patient so that an appropriate inspiratory waveform or other ventilatory parameters might be selected and utilized. Further, the emphasis in prior studies has been to attempt to determine the "best" single pressure or flowrate inspiratory waveform for all types of lung conditions, even though the characteristics and behavior of lungs afflicted with emphysema, asthma and acute respiratory distress syndrome, for example, are very different.

SUMMARY OF THE INVENTION

It is therefore among the objectives of this invention to provide a methodology for operating a ventilation apparatus and/or anesthesia system for use with patients having a variety of lung conditions, which attempts to equalize the distribution of ventilation in lungs with unequal resistance and/or unequal compliance, and, which minimizes the mean lung pressure over time.

These objectives are accomplished in a methodology which includes determining the class of the lungs of a given patient, selecting a pressure or flowrate waveform and other ventilatory parameters such as inspiratory pause and inspiratory time which are appropriate for that lung class, and then ventilating the patient with the selected inspiratory waveform and ventilatory parameters. New ventilation inspiratory waveforms are provided which have been found to be advantageous for certain types of lung classes. An inspiratory pause is generated by imposing a zero flowrate condition in the trachea or endotracheal tube (ETT).

One aspect of this invention is predicated upon the concept of determining the particular class of the lungs of a particular patient. There aie a total of 16 possible variations of lung types, given that each lung of a patient has a certain left and right compliance and a certain left and right resistance. It has been determined through computer modeling and mathematical derivation, that these 16 lung types can be categorized into three general lung classes, including: (1) Class I: lungs having equal individual time constants, where the time constant of each lung is the product of its resistance and compliance; (2) Class II: lungs of unequal compliance, with no restriction on resistance; and, (3) Class III: lungs of equal compliance but unequal resistance. The lung classification scheme of this invention depends on the ability to identify for each patient which of the three general lung classes mentioned above is applicable so that an appropriate inspiratory waveform and other ventilatory parameters such as inspiratory time and pause can be selected.

Clinical determination of the different lung classes is accomplished in the method of this invention using one or more algorithms generated by modified control software of commercially available computer-controlled ventilators.

One algorithm employs a constant (or any other) flowrate waveform wherein the time of inspiration is varied from a shorter time period to a longer time period, e.g. two seconds to four seconds, while maintaining all other ventilatory parameters constant. A measurement is taken of the end-tidal carbon dioxide concentration following exhalation after the shorter, two second inspiratory time, and then a second measurement of end-tidal carbon dioxide is taken upon exhalation after at least ten breaths or one minute at the longer, four second inspiratory time. In Class III lungs, it is believed that a substantial decrease in end-tidal carbon dioxide concentration will occur following ventilation for at least ten breaths or one minute with an increased inspiratory time. This is because it is believed that a better ventilation distribution ratio is obtained using a constant flowrate waveform with Class III lungs wherein the inspiratory time is increased. In turn, a better ventilation distribution ratio leads to better washout, which then leads to lower end tidal carbon dioxide concentration. Class I and II lungs, on the other hand, are believed to show no decrease, or an increase, in end-tidal carbon dioxide concentration following exhalation under the same inspiratory time and tidal volume parameters. As a result, a Class III lung may be identified and distinguished from Class I and II lungs using this algorithm.

A second algorithm to detect Class III lungs involves the use of a newly implemented inspiratory waveform, a rising exponential flowrate inspiratory waveform, with an inspiratory pause (e.g., 25% of inspiratory time). It has been determined mathematically and by computer simulation that the ventilation distribution ratio for Class III lungs is substantially improved using a rising exponential flowrate inspiratory waveform where an inspiratory pause is employed, compared to the same waveform when there is no inspiratory pause. It is believed that a decrease in end-tidal carbon dioxide will occur following ventilation for at least ten breaths or one minute with the inspiratory pause compared to ventilation with the preceding waveform without the inspiratory pause. No lowering of end-tidal carbon dioxide is expected in a Class I lung under similar ventilatory parameters, and there is either an increase or no change in end-tidal carbon dioxide for Class II lungs under the same circumstances.

A third algorithm can be employed to identify Class III lungs which involves the use of a constant pressure waveform followed immediately by ventilation for at least ten breaths or one minute with a rising exponential flowrate waveform, wherein both waveforms have the same tidal volume and inspiratory time. When using these consecutive waveforms on a patient with Class III lungs, it is believed that an increase of end-tidal carbon dioxide would follow inflation with the rising exponential flowrate waveform. No such change is expected for either Class I or Class II lungs, and therefore a Class III lung may be positively identified with this algorithm.

In addition to identifying the class of lungs by measuring the end-tidal carbon dioxide concentration, the method and apparatus of this invention contemplates lung class identification by the measurement of the intratracheal pressure trace. The intratracheal pressure trace is obtained by sampling the pressure at the distal tip of the endotracheal tube using a pressure sensor pneumatically connected to a pressure coupling port or lumen located at the distal tip of the endotracheal tube with which the patient is intubated. An inspiratory pause is added during mechanical ventilation to assist in identifying the lung class. In the presently preferred embodiment, the intratracheal pressure trace is divided into segments corresponding to different phases of inspiration, i.e., active inflation, inspiratory pause, beginning of expiration, and, end of expiration using the flow and pressure trace signals. Different algorithms, described in detail below, are then applied to the intratracheal pressure trace segments.

It has been observed that it is possible to differentiate between a Class I lung, and Class II or III lungs, by the intratracheal pressure trace during inspiration. A Class I lung exhibits a linear intratracheal pressure trace whereas Class II or Class III lungs have a non-linear pressure trace during active inflation, using a constant flowrate waveform. Such characteristics have been observed both with mechanical models and computer simulations of two compartment lungs. Importantly, it has been observed that Class III lungs can be readily identified by examining the intratracheal pressure trace during the inspiratory pause. By definition, there is no flow within an endotracheal tube during a true inspiratory pause. The volumes in the lung compartments can then redistribute according to the pressure differentials during the inspiratory pause. It has been observed that for Class III lungs, the pressure trace during inspiratory pause has a slowly decaying slope, whereas the pressure traces for Class I or II lungs quickly drop in a step fashion from a peak inspiratory pressure to a plateau. A Class III lung can thus be clearly distinguished from Class I and II lungs in this manner.

An examination of the intratracheal pressure trace during expiration is also helpful in identifying and differentiating between the different lung classes. It has been observed that for a Class II lung, the intratracheal pressure trace during exhalation follows two different time constants. The shorter time constant predominates at the start of exhalation and quickly dies out, while the longer time constant persists and dominates toward the end of exhalation. Software within the apparatus of this invention takes the natural logarithm of the intratracheal pressure trace at the beginning and ending segments of exhalation, and samples the resulting slopes of the natural logarithms over time. It has been determined that if the slopes are markedly different, then the lung class is not a Class I lung, but could be a Class II or III lung. Using the inspiratory pause intratracheal pressure trace described above, a Class III lung can be positively identified as compared to a Class I or II lung. Consequently, Class I, II and III lung types can be differentiated from one another using a combination of the intratracheal pressure traces during expiration and during inspiratory pause.

Still another method of assisting in determining the lung characteristics of a particular patient involves quantification of the effective time constant of the entire respiratory system. In the presently preferred embodiment, a constant pressure waveform (pressure step input of time duration $T_i$) is applied at the carina and an analysis is undertaken of the resulting flow rate trace at the distal tip of the endotracheal tube. To obtain a constant pressure waveform at the carina, the pressure is sampled at the distal tip and a feedback loop within the apparatus herein is implemented to maintain the pressure thereat to the desired constant value. The flowrate at the distal tip of the endotracheal tube over time ($Q_{ett}(t)$) decays exponentially in response to a pressure step at the carina, with the maximum inspiratory flowrate, $Q_{max}$, corresponding to the initial flowrate, $Q_{ett}(t=0)$. The point in time at which $Q_{ett}(t)$ equals $\exp(-1) \cdot Q_{max}(0.368\ Q_{max})$ corresponds to the time constant of the entire respiratory system, and can be determined by measuring the flow at the endotracheal tube with the flow meter placed thereat.

Alternatively, the effective time constant of the entire respiratory system can also be quantified by an increasing ramp pressure input at the carina. For an increasing pressure waveform, $Q_{max}=Q_{ett}(T_i)$. The point in time when $Q_{ett}(t)$ reaches $(1-\exp(-1))(Q_{max})=(1-0.368)Q_{max}=0.632\ Q_{max}$ is the time constant of the entire respiratory system and can be determined in the same way as with the constant pressure technique.

Once the class of the lungs of a given patient has been determined by employing one or more of the algorithms discussed above, an appropriate inspiratory waveform and other ventilatory parameters can be selected which are best suited for that lung classification. Another aspect of this invention is predicated upon the concept that different types of inspiratory waveforms and ventilatory parameters are more appropriate for different classes of lungs than others, and, in fact, some types of inspiratory waveforms can be harmful when used with patients having certain lung conditions. Keeping in mind that the goal is to obtain a ventilation distribution ratio which approaches unity with lungs of different time constants, while minimizing the mean lung pressure, it has been found that the rising exponential inspiratory waveform is preferred in most instances except for Class III lungs. A constant pressure inspiratory waveform, for example, while it causes the ventilation distribution ratio to approach 1.0 for a Class III lung, may not be indicated for certain patients with Class III lungs because it has been found to increase mean lung pressure in such patients. Further, longer inspiratory times and the use of an inspiratory pause provide a more even ventilation distribution ratio in Class III lungs. With respect to Class I and Class II lungs, inspiratory waveforms whose time derivatives are strong functions of time are recommended to obtain more even ventilation distribution ratios and reduced mean lung pressures. The use of an inspiratory pause is not recommended for either Class I or Class II lungs because it increases mean lung pressure and/or produces a more uneven ventilation distribution ratio.

The appropriately selected ventilation inspiratory waveform and other ventilatory parameters such as inspiratory time and inspiratory pause, are then used to ventilate the patient and deliver either oxygen or a combination of oxygen with any of air, helium, nitrous oxide, nitric oxide, and anesthetics. Because the ventilation distribution ratio is improved with the method of this invention, a more efficient and effective mass transfer occurs at the blood/gas interface within the lungs. Further, the mean lung pressure is reduced to minimize interference with cardiac output.

DESCRIPTION OF THE DRAWINGS

The structure, operation and advantages of the presently preferred embodiment of this invention will become further apparent upon consideration of the following description, taken in conjunction with the accompanying drawings, wherein.

FIG. 5 is a table of a computer simulation for normal and healthy lung configurations with equal resistances, compliances and time constants wherein:

$R_r$=6 cm $H_2O$/l/s $C_r$=0.025 l/cm $H_2O$ $R_l$=6 cm $H_2O$/l/s $C_l$=0.025 l/cm $H_2O$

FIG. 6 is a table of a computer simulation of lungs having equal resistances, unequal compliances and unequal time constants, wherein:

$R_r$=6 cm $H_2O$/l/s $C_r$=0.0125 l/cm $H_2O$ $R_l$=6 cm $H_2O$/l/s $C_l$=0.025 l/cm $H_2O$

FIG. 7 is a table of a computer simulation of lungs having unequal resistances, equal compliances and unequal time constants, wherein:

$R_r$=6 cm $H_2O$/l/s $C_r$=0.0125 l/cm $H_2O$ $R_l$=12 cm $H_2O$/l/s $C_l$0.025 l/cm $H_2O$

FIG. 8 is a table of a computer simulation of lungs having unequal resistances and unequal time constants, where the compliance of the right lung is less than that of the left lung, and wherein:

$R_r$=6 cm $H_2O$/l/s $C_r$=0.0125 l/cm $H_2O$ $R_l$=12 cm $H_2O$/l/s $C_l$=0.025 l/cm $H_2O$

FIG. 9 is a table of a computer simulation of lungs similar to those of FIG. 8 except with the compliance of the right lung being greater than the compliance of the left lung and unequal time constants, wherein:

$R_r$=6 cm $H_2O/l/s$
$C_r$=0.0375 l/cm $H_2O$
$R_l$=12 cm $H_2O/l/s$
$C_l$=0.0125 l/cm $H_2O$

FIG. 10 is a table of a computer simulation of lungs which cannot be characterized as "normal and healthy" but whose abnormalities do not manifest themselves as inequalities in time constants. The inequalities in resistances and compliances are such that the time constants of the right and left lungs are equal, and wherein:

$R_r$=6 cm $H_2O/l/s$
$C_r$=0.025 l/cm $H_2O$
$R_l$=12 cm $H_2O/l/s$
$C_l$=0.0125 l/cm $H_2O$

Figure 12:
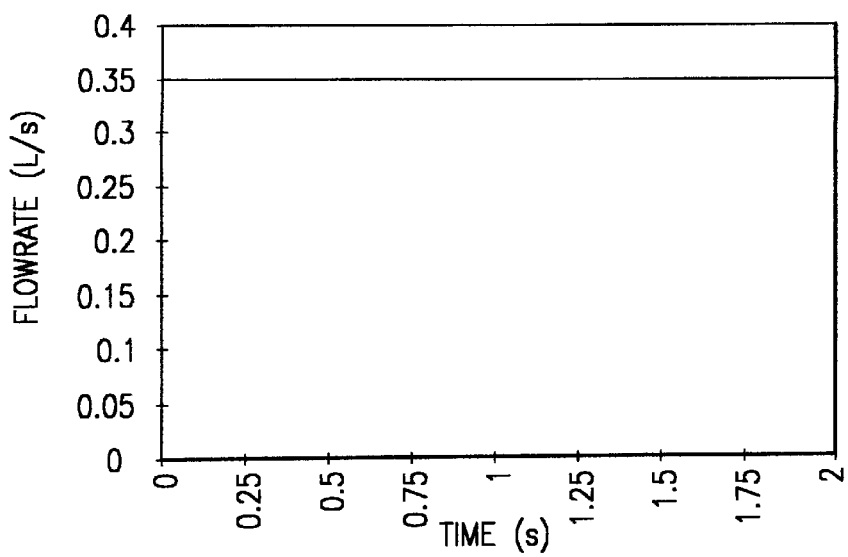
Figure 13:
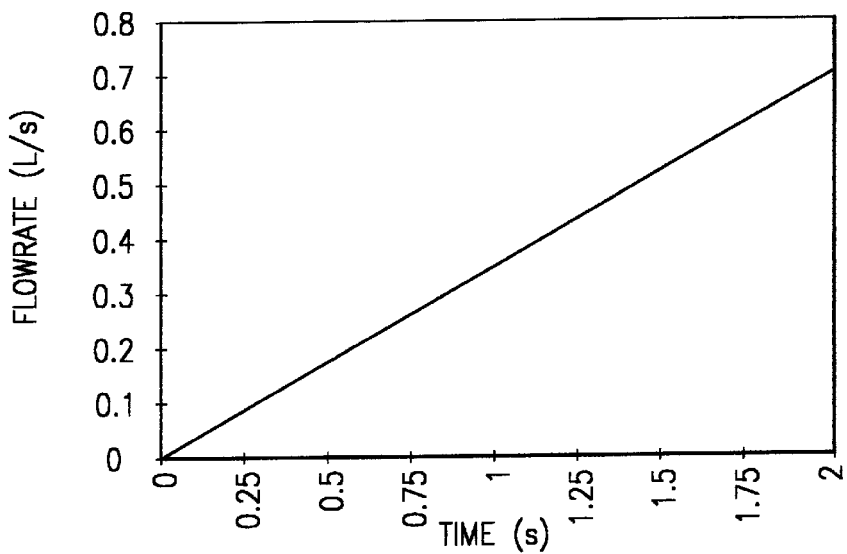
Figure 14:
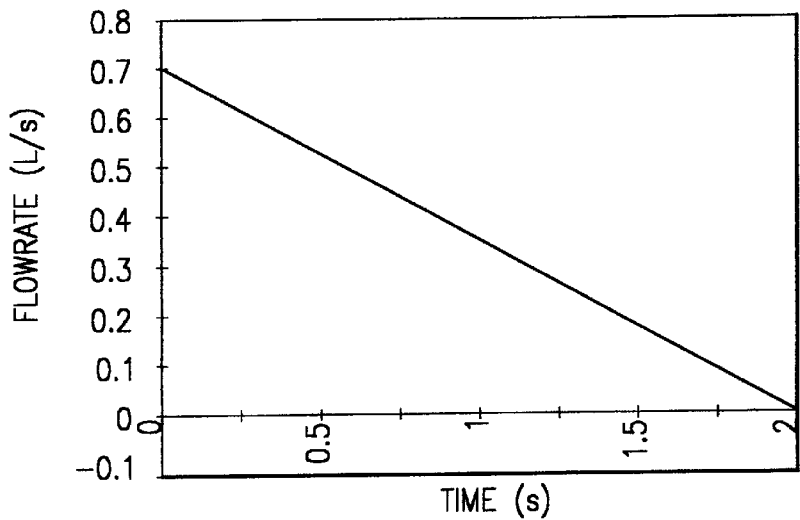
Figure 15:
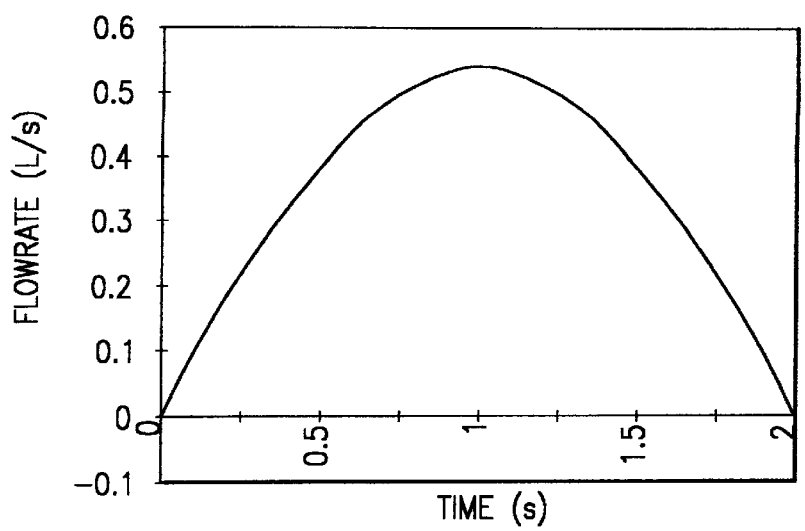
Figure 16:
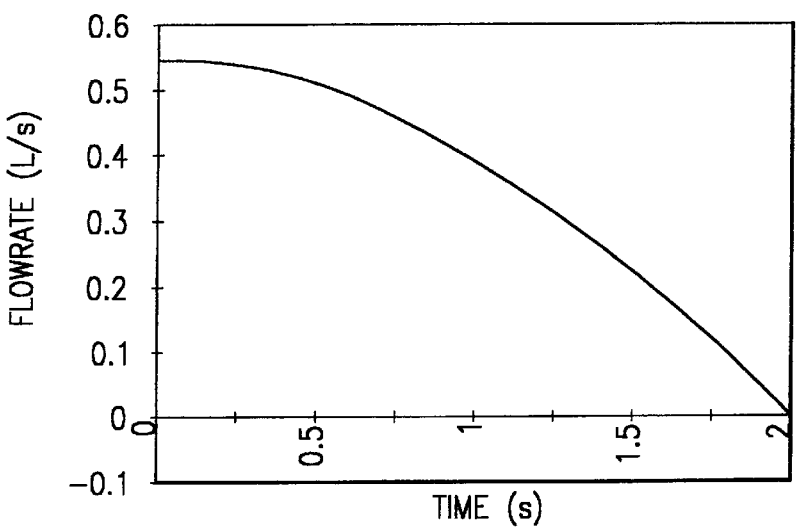
Figure 17:
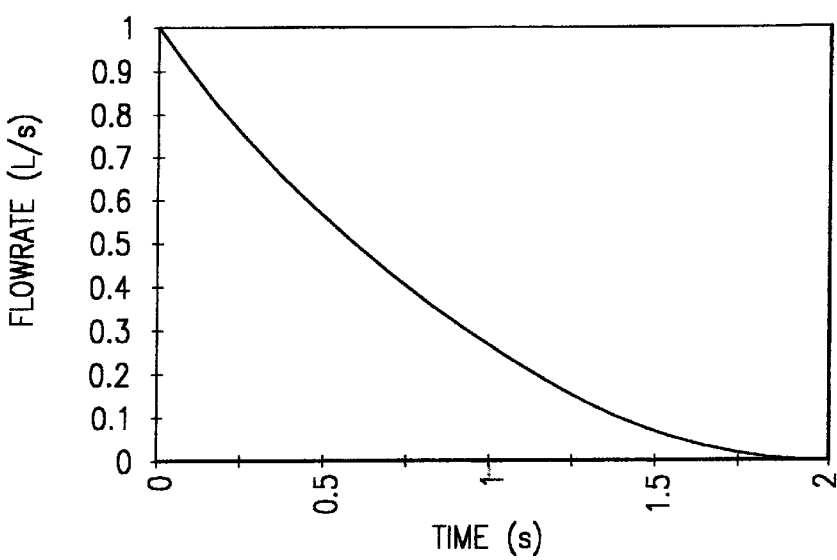
Figure 18:
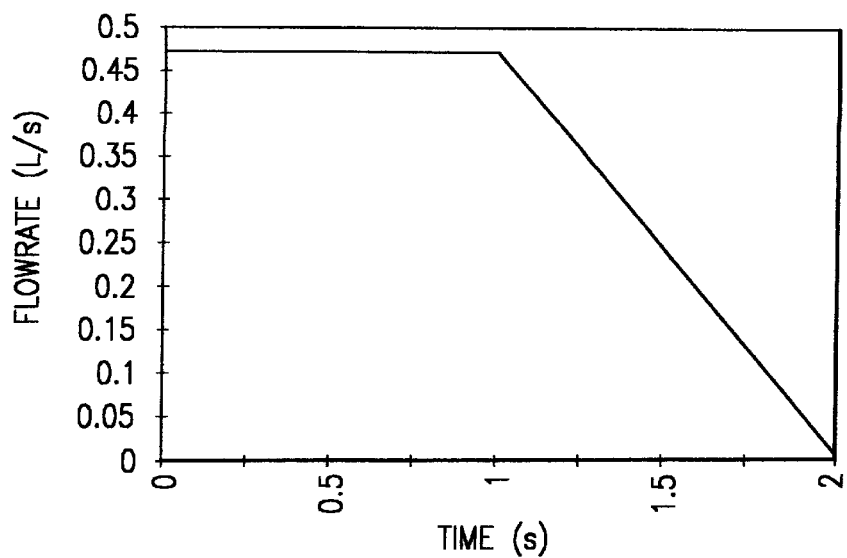
Figure 19:
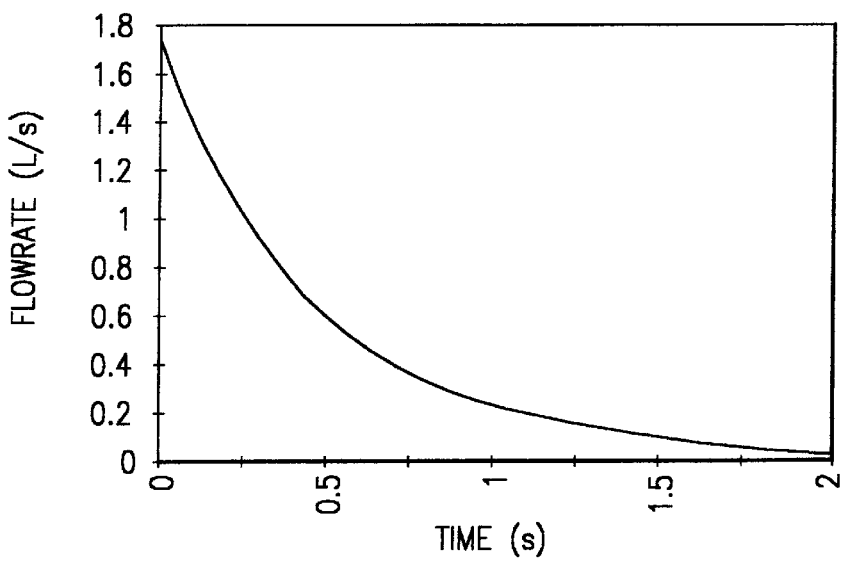
Figure 20:
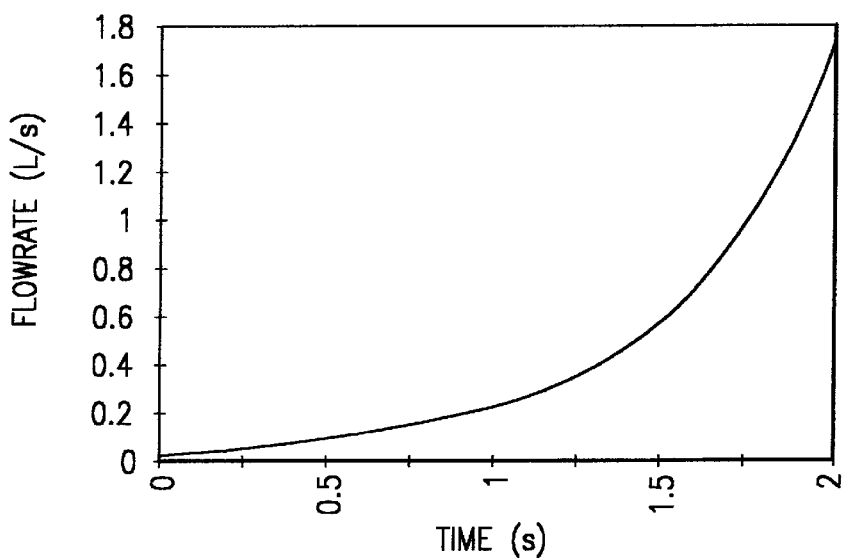
Figure 21:
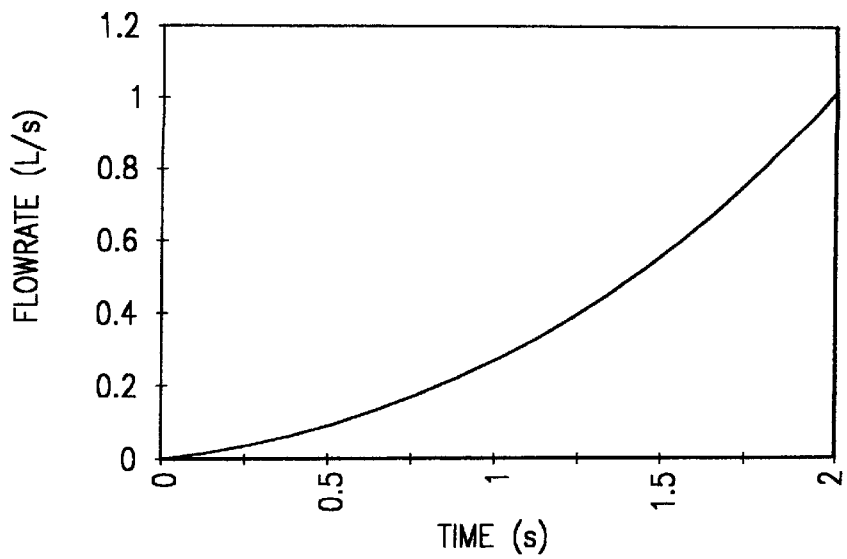
Figure 22:
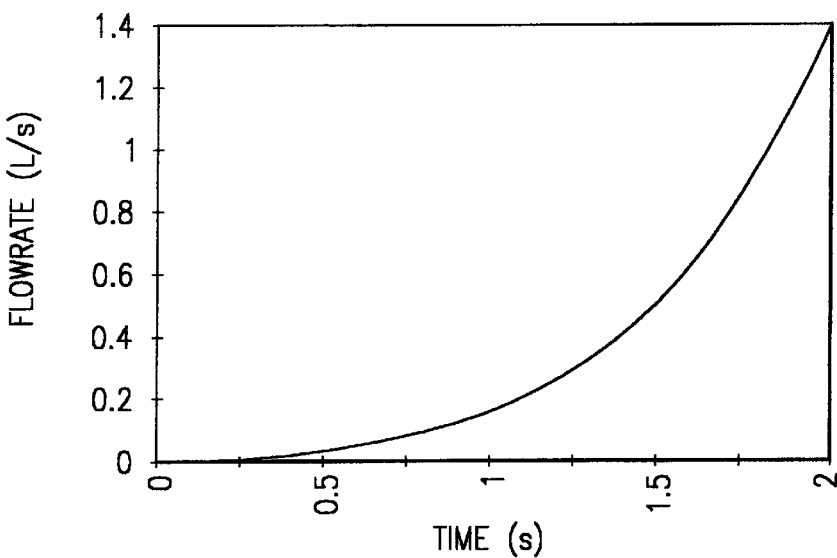
Figure 23:
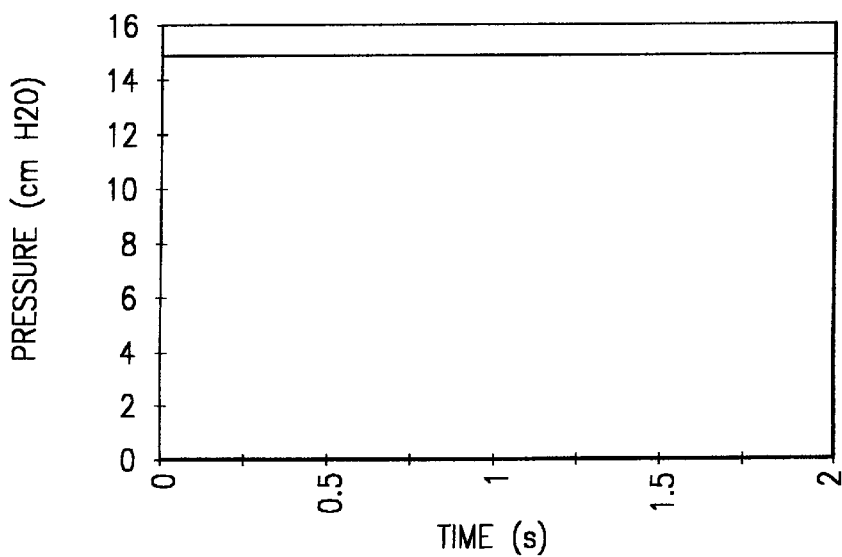
Figure 24:
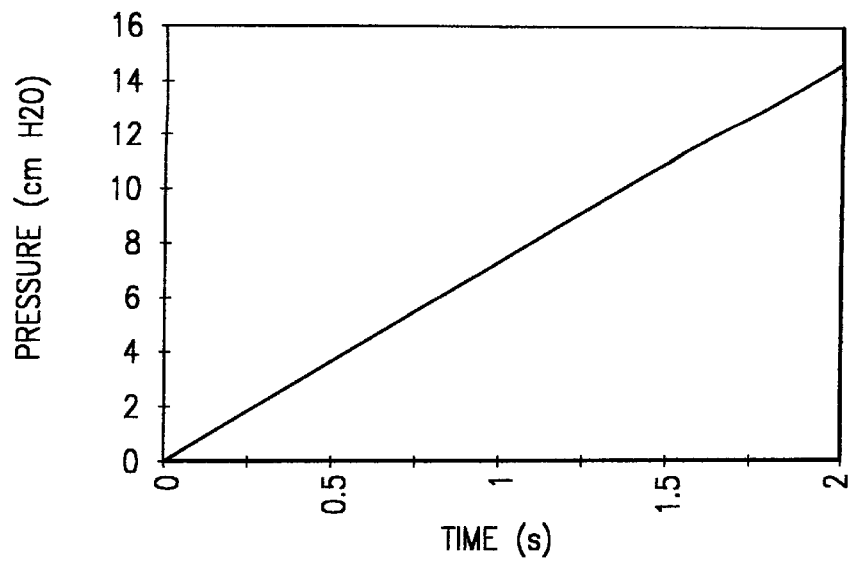
Figure 25:
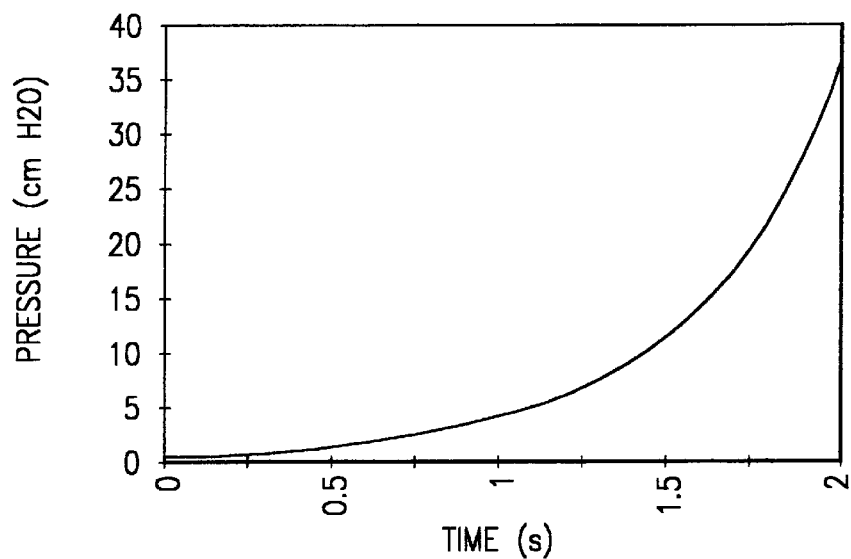
Figure 26:
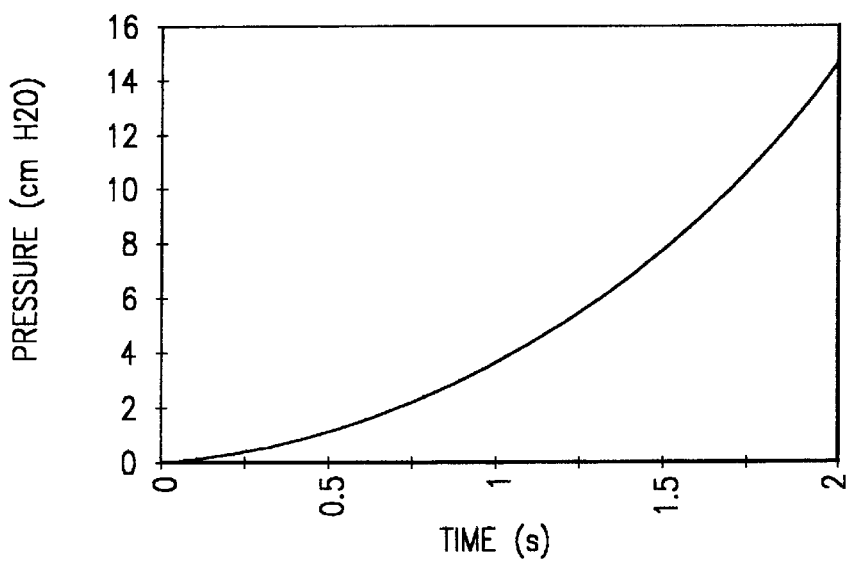
Figure 27:
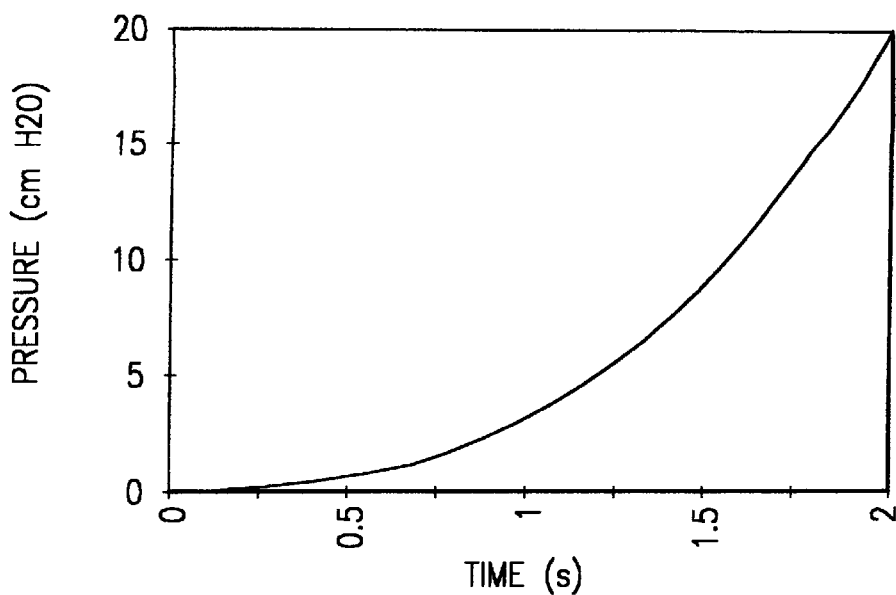

FIG. 11 is a condensed table of the results of the computer simulations shown in FIGS. 5–10 in which the qualitative trends and effects on different lung configuration types is emphasized in narrative form; and FIG. 12 is a graphical illustration of a constant flowrate inspiratory waveform, having an ordinate which depicts flowrate in liters per second (L/S) and an abscissa depicting time (t) in seconds;

FIG. 13 is a graphical illustration of an increasing flowrate inspiratory waveform, having an ordinate which depicts flowrate in liters per second (L/S) and an abscissa depicting time (t) in seconds;

FIG. 14 is a graphical illustration of a decreasing flowrate inspiratory waveform, having an ordinate which depicts flowrate in liters per second (L/S) and an abscissa depicting time (t) in seconds;

FIG. 15 is a graphical illustration of a half-sine (o–π) flowrate inspiratory waveform, having an ordinate which depicts flowrate in liters per second (L/S) and an abscissa depicting time (t) in seconds;

FIG. 16 is a graphical illustration of a quarter-sine (π2–π) flowrate inspiratory waveform, having an ordinate which depicts flowrate in liters per second (L/S) and an abscissa depicting time (t) in seconds;

FIG. 17 is a graphical illustration of a shifted quarter-sine (π–3π/2) flowrate inspiratory waveform, having an ordinate which depicts flowrate in liters per second (L/S) and an abscissa depicting time (t) in seconds;

FIG. 18 is a graphical illustration of a trapezoid flowrate inspiratory waveform, having an ordinate which depicts flowrate in liters per second (L/S) and an abscissa depicting time (t) in seconds;

FIG. 19 is a graphical illustration of a decaying exponential flowrate inspiratory waveform having a time constant of flowrate change, τ, equal to the inspiratory time divided by 5, $t_i/5$. The graph has an ordinate which depicts flowrate in liters per second (L/S) and an abscissa depicting time (t) in seconds;

FIG. 20 is a graphical illustration of a rising exponential flowrate inspiratory waveform having a time constant of flowrate change, τ, equal to the inspiratory time divided by 5, $t_i/5$. The graph has an ordinate which depicts flowrate in liters per second (L/S) and an abscissa depicting time (t) in seconds;

FIG. 21 is a graphical illustration of a time squared flowrate inspiratory waveform, having an ordinate which depicts flowrate in liters per second (L/S) and an abscissa depicting time (t) in seconds;

FIG. 22 is a graphical illustration of a time cubed flowrate inspiratory waveform, having an ordinate which depicts flowrate in liters per second (L/S) and an abscissa depicting time (t) in seconds;

FIG. 23 is a graphical illustration of a constant pressure inspiratory waveform, having an ordinate which depicts pressure in centimeters of water (cm $H_2O$) and an abscissa depicting time (t) in seconds;

FIG. 24 is a graphical illustration of an increasing pressure inspiratory waveform, having an ordinate which depicts pressure in centimeters of water (cm $H_2O$) and an abscissa depicting time (t) in seconds;

FIG. 25 is a graphical illustration of a rising exponential pressure inspiratory waveform having a time constant of pressure rise, τ, equal to inspiratory time divided by five, $t_i/5$, and a $P_o$ equal to 0.25 where $P_o$ is an arbitrarily set starting point for the pressure waveform which is iteratively adjusted as the pressure waveform is maintained, and as the actually delivered tidal volume is measured, until the desired tidal volume is obtained. The graph has an ordinate which depicts pressure in centimeters of water (cm $H_2O$) and an abscissa depicting time (t) in seconds;

FIG. 26 is a graphical illustration of a time squared pressure inspiratory waveform, having a $P_o$ equal to 15 where $P_o$ is an arbitrarily set starting point for the pressure waveform which is iteratively adjusted as the pressure waveform is maintained, and as the actually delivered tidal volume is measured, until the desired tidal volume is obtained. The graph has an ordinate which depicts pressure in centimeters of water (cm $H_2O$) and an abscissa depicting time (t) in seconds; and FIG. 27 is a graphical illustration of a time cubed pressure inspiratory waveform having a $P_o$ equal to 20 where $P_o$ is an arbitrarily set starting point for the pressure waveform which is iteratively adjusted as the pressure waveform is maintained, and as the actually delivered tidal volume is measured, until the desired tidal volume is obtained. The graph has an ordinate which depicts pressure in centimeters of water (cm $H_2O$) and an abscissa depicting time (t) in seconds.

DETAILED DESCRIPTION OF THE INVENTION

The overall objectives of this invention are to improve the mass transfer rate and efficiency at the blood/gas interface of the lungs in both directions, i.e. removal of carbon dioxide and anesthetics and inflow of oxygen and anesthetics, while minimizing the mean or average pressure in the lungs during ventilation. In order to achieve these objectives, an analysis is disclosed resulting in the grouping of a number of lung types into three general, main classes. Algorithms are provided to permit a determination in a clinical setting of the particular classification for the lungs of a given patient. Finally, a number of new inspiratory waveforms are disclosed which can be utilized with other ventilatory parameters to ventilate a patient with a particular lung classification to achieve an improved ventilation distribution ratio while minimizing mean lung pressure.

The following discussion is divided into sections directed to the lung classification analysis, clinical determination of the lung class of a particular patient, and, the selection and use of appropriate inspiratory waveforms and other ventilatory parameters for different lung classes.

Development of Lung Classification

Figure 1:
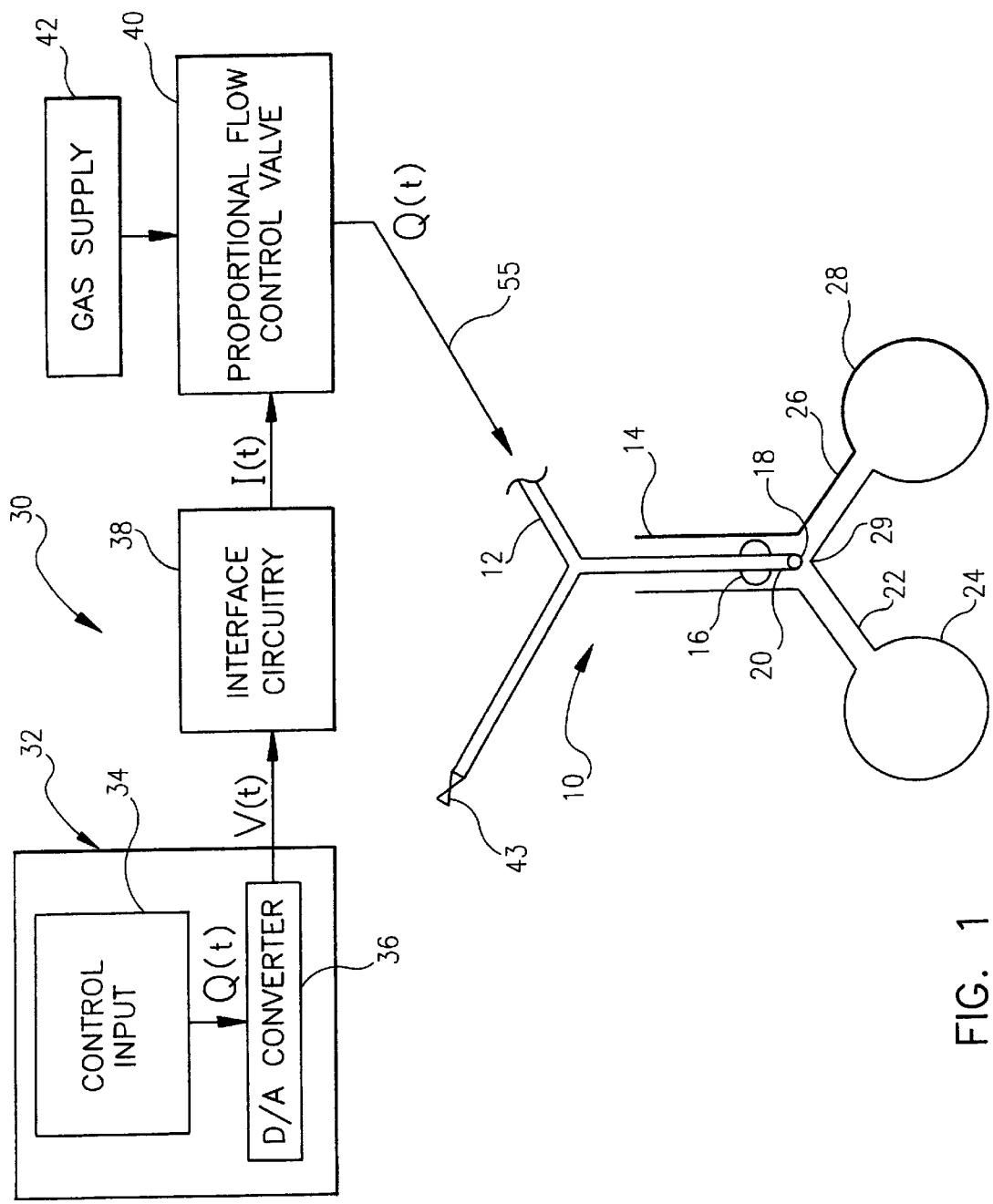
FIG. 1 is a schematic view of an open loop ventilation system capable of providing flowrate waveform shaping during mechanical inspiratory.

With reference initially to the bottom portion of FIG. 1, a schematic depiction is provided of the respiratory passageways of a patient who has been intubated with an endotracheal tube 10 connected to a Y-piece 12. The endotracheal tube 10 is inserted within the trachea 14 of the patient, and a cuff 16 provided on the exterior surface of endotracheal tube 10 is inflated to create a seal with the trachea 14. As described below, one or more sensors 18 sample pressure and gas composition at sampling ports located at the distal tip 20 of the endotracheal tube 10 to provide measurements of pressure and end-tidal carbon dioxide content. One type of endotracheal tube 10 suitable for use herein is a "Hi-Lo" endotracheal tube commercially available from Mallinckrodt. Such tube includes sampling ports at the distal tip which can be pneumatically connected to pressure sensors.

For purposes of the present discussion, the left bronchus 22 and left lung 24 will be referred to as one respiratory passageway, and the right bronchus 26 and right lung 28 forms another respiratory passageway. The bronchi 22, 26 meet at the carina 29 where the distal tip 20 of the endotracheal tube 10 is positioned. The term "resistance" as used herein is meant to refer to the flow resistance or restriction within each respiratory passageway. The term "compliance" refers to the flexibility or elasticity of the left and right lungs 24, 28 as they expand and contract during inspiration.

Figure 4:
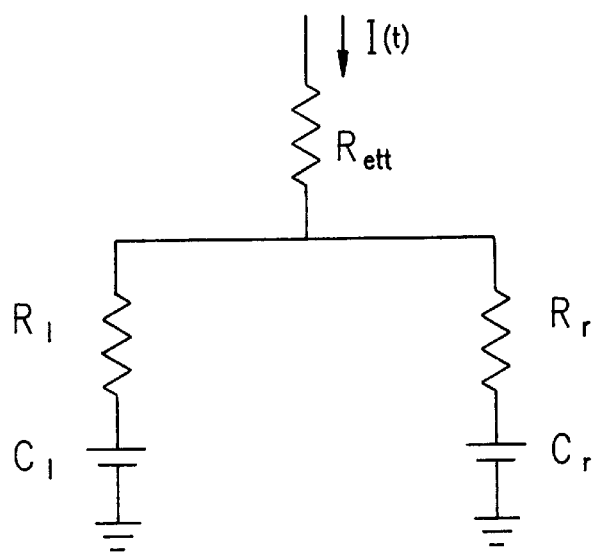
FIG. 4 is a schematic electrical circuit depicting an electrical analogy to the respiratory pathways formed by the bronchi and lungs of a patient, which is utilized to provide mathematical modeling of the effects of resistance and compliance on distribution of pulmonary ventilation.

Development of the lung classes of this invention began with a computer model based on the mathematical model first suggested by Otis et al. in *Mechanical Factors and Distribution of Pulmonary Ventilation, Journal of Applied Physiology* 8:427, 1956. The work of Otis, et al. established that an electrical analogy could be employed to model the behavior of lungs wherein compliance equals capacitance, and flow resistance equals electrical resistance. Thus, the diagram depicted in FIG. 4 illustrating an electrical circuit with resistances $R_{ett}$, $R_l$ and $R_r$, and capacitances $C_l$ and $C_r$, with an input I(t), is electrically analogous to the respiratory airways of an intubated patient. The resistance $R_{ett}$ is analogous to the flow resistance within an endotracheal tube, the resistances $R_l$ and $R_r$ are analogous to the flow resistances within the respective bronchi of a patient, and, the capacitances $C_l$ and $C_r$ are analogous to the compliances of the left and right lungs.

A computer program was developed to simulate and analyze the effects of inspiratory waveform shape, inspiratory time ($T_i$), inspiratory pause (IP) and tidal volume (VT) during mechanical ventilation. In order to utilize the model proposed by Otis et al. and shown in FIG. 4, it was assumed that compliances and flow resistances are linear, particularly in situations where the total lung volume is less than two (2) liters above functional residual capacity (FRC) and the inspiratory flowrates are less than 80 liters per minute. The term "functional residual capacity," or FRC, refers to the volume of air left in the lungs after exhalation.

Figure 3:
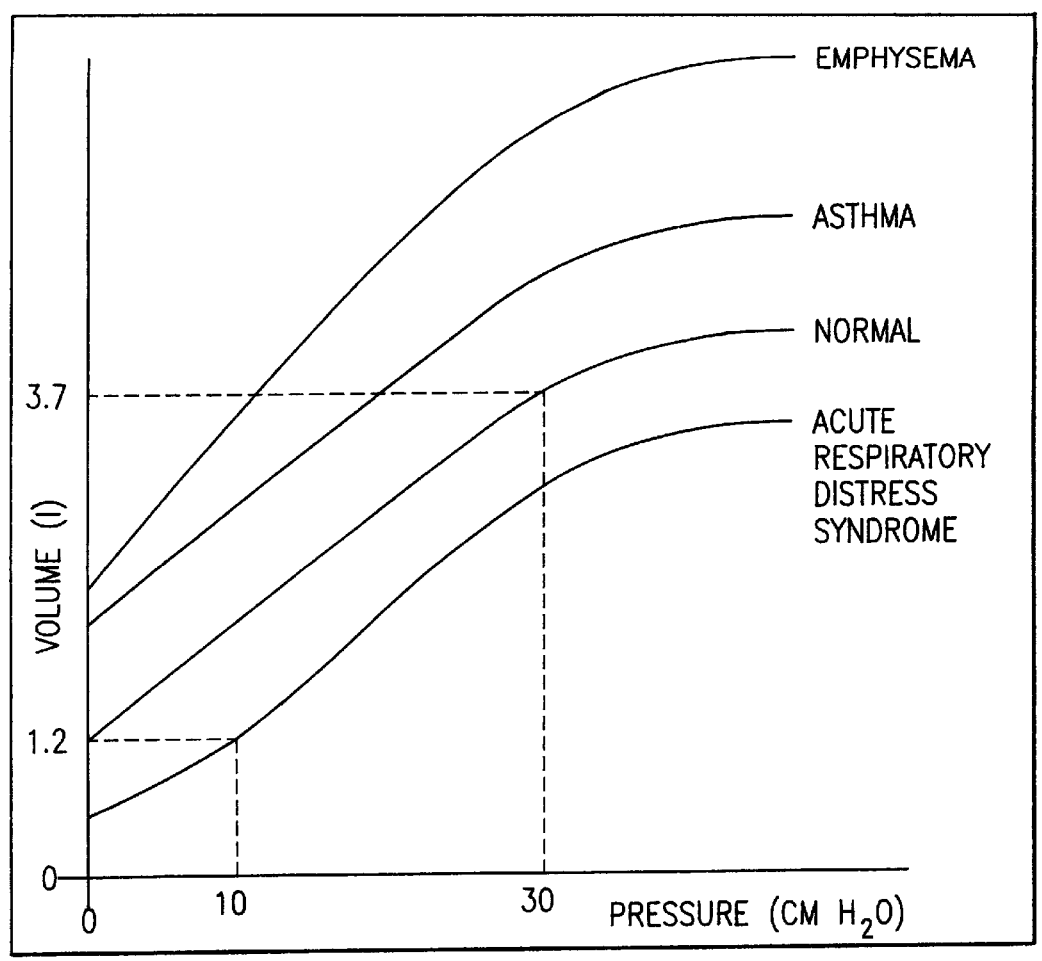
FIG. 3 is a graphical depiction of compliance curves for normal and diseased lungs wherein "FRC" is the functional residual capacity and "PEEP" is positive end expiratory pressure.

With reference to FIG. 3, the propriety of assuming linear compliances and resistances is graphically depicted. The lung compliance curve for a healthy, anesthetized patient in the supine position is a highly skewed sigmoid with a wide linearly sloping portion that flattens out at the top of the curve as the elastic limit of the lungs is approached. See Nunn, J. F. *Applied Respiratory Physiology* (Third Edition), London, Butterworths 1987. The inflection point where the compliance curve departs from linearity is approximately at the 30 cm $H_2O$ and 2.5 liters above FRC coordinate, for healthy, anesthetized patients in a supine position. Accordingly, the assumption that compliance is linear for healthy anesthetized patients in a supine position, for tidal volumes not exceeding 2 liters, is accurate.

With respect to patients having lungs with some pathology, or, indeed, serious medical conditions, additional curves are provided in FIG. 3 depicting volume vs. pressure plots for patients having emphysema, asthma and acute respiratory distress syndrome. It can be observed that the compliance curves still retain their skewed sigmoidal shape although the scale and the degree of skew are different. Therefore, the assumption of a linear compliance for these "abnormal" lungs can also be made, provided the volume in the lung is below the inflection point. As depicted in FIG. 3, the inflection points of the compliance curves for different lung pathologies follow a roughly diagonal locus that runs from the upper left to the bottom right of the volume vs. pressure plot. As a practical matter, the inflection point locus implies that a less compliant lung will top its curve at a lower volume above FRC compared to a normal lung. Because it is less compliant, the stiffer lung will generally receive less volume than a more compliant lung in proportion to the ratio of the compliances between the two lungs. Consequently, the very nature of the less compliant lung tends to prevent it from topping its curve and thus stay within the linear compliance region. Conversely, the more compliant lung accepts more volume but also tops its curve at a higher volume above FRC and will thus stay within the linear portion of its compliance curve for a larger volume range. Accordingly, the assumption of linear compliances and resistances for the various types of lung conditions depicted in FIG. 3 is valid and practically useful within the parameters of total lung volume less than 2 liters above FRC, and inspiratory flowrates less than 80 liters per minute.

As noted above, the computer model is intended to simulate and analyze the effects of (1) inspiratory waveform shape, (2) inspiratory time, $T_i$, (3) inspiratory pause, (IP), and (4) tidal volume, (VT) during mechanical ventilation on lungs having a variety of resistance and compliance parameters. Prior to this invention, four inspiratory waveforms had been utilized in ventilation and anesthesia apparatus which can be described in equation form as follows:

Constant Flowrate: (1)
$$Q_{ett}(t) = \frac{VT}{T_i}$$

Increasing Flowrate: (2)
$$Q_{ett}(t) = \frac{2VT}{T_i^2} \cdot t$$

Decreasing Flowrate: (3)
$$Q_{ett}(t) = -\frac{2VT}{T_i^2} \cdot t + 2\frac{VT}{T_i}$$

Half-Sine $(0-\pi)$ Flowrate: (4)
$$Q_{ett}(t) = \frac{\pi VT}{2T_i} \cdot \sin\left(\frac{\pi}{T_i} \cdot t\right)$$

Where:

$Q_{ett}(t)$=total flowrate at the trachea, or endotracheal tube, over time

VT=tidal volume $T_i$=inspiratory time t=time

In addition to these four known waveforms, a number of new flowrate waveforms have been discovered which, in at least some instances, produce improved results as discussed in more detail below.

Quarter sine $(\pi/2 - \pi)$ (5)

$$Q_{ett}(t) = \frac{\pi VT}{2T_i} \sin\left(\frac{\pi}{2} + \frac{\pi}{2T_i} \cdot t\right)$$

Shifted Quarter Sine $(\pi - 3\pi/2)$ (6)

$$Q_{ett}(t) = \frac{VT}{T_i \cdot \left(1 - \frac{2}{\pi}\right)} \left(1 + \sin\left(\pi + \frac{\pi}{2T_i} t\right)\right)$$

Trapezoid (7)

$$Q_{ett}\left(0 \le t < \frac{T_i}{2}\right) = \frac{4VT}{3T_i}$$

$$Q_{ett}\left(\frac{T_i}{2} \le t \le T_i\right) = -\frac{8VT}{3T_i^2} \cdot \left(t - \frac{T_i}{2}\right) + \frac{4VT}{3T_i}$$ (8)

Decaying Exponential $(\tau = T_i/5)$ (9)

$$Q_{ett}(t) = \frac{VT}{0.198652T_i} e^{-\frac{5t}{T_i}}$$

Decaying Exponential $(\tau = T_i/n)$ (10)

$$Q_{ett}(t) = f[VT, T_i] e^{\frac{-nt}{T_i}}$$

Rising Exponential $(\tau = T_i/5)$ (11)

$$Q_{ett}(t) = \frac{0.033918 VT}{T_i} e^{-\frac{5t}{T_i}}$$

Rising Exponential $(\tau = T_i/n)$ (12)

$$Q_{ett}(t) = f[VT, T_i] e^{\frac{nt}{T_i}}$$

$t^2$ (13)

$$Q_{ett}(t) = \frac{3VT \cdot t^2}{T_i^3}$$

$t^3$ (14)

$$Q_{ett}(t) = \frac{4VT \cdot t^3}{T_i^4}$$

$t^n$ (15)

$$Q_{ett}(t) = \frac{(n+1)VT}{T_i^{n+1}} \cdot t^n$$

Where:

$Q_{ett}(t)$=total flowrate at the trachea, over time
VT=tidal volume
$T_i$=inspiratory time
$\tau$=time constant of flowrate change
n=any number
f[VT, $T_i$]=a constant which is a function of VT and $T_i$
t=time Additionally, an ideal increasing exponential flowrate waveform is given by the following relationship:

$$Q_{ett}(t) = Ae^{\alpha t}$$ (16)

Where:

$$A = \frac{\alpha}{e^{\alpha T_i} - 1} VT$$ (17)

$$\alpha = \frac{|C_l - C_r|}{C_r C_l |(R_l - R_r)|}$$ (18)

$C_r$=right lung compliance
$C_l$=left lung compliance
$R_r$=right lung resistance
$R_l$=left lung resistance
VT=tidal volume
$T_i$=inspiratory time
$Q_{ett}(t)$=total flowrate of trachea or endotracheal tube, over time
t=time It should be noted that equations 9 and 11 listed above, i.e. for decaying exponential and rising exponential flowrate waveforms, employ a time constant equal to the inspiratory time divided by 5 ($T_i/5$.) This was an arbitrary selection utilized in the computer model for purposes of comparison with other waveforms. Other time constants of the flowrate decay can be utilized, e.g. $\tau = T_i/n$, where n can be essentially any number. Equations 10 and 12 depict decaying exponential and rising exponential flowrate waveforms where $\tau = T_i/n$, and wherein the constant f [VT, $T_i$] is a function of tidal volume (VT) and inspiratory time ($T_i$).

In addition to the flowrate inspiratory waveform noted above, shaping of a particular input to a patient can be achieved with pressure inspiratory waveforms. With waveforms of this type, the clinician is concerned with determining the peak pressure required during each breath to deliver the desired tidal volume (VT) to the patient within a chosen inspiratory time ($T_i$). For purposes of the computer modeling employed in this invention to obtain data for lung classification, as described below, three pressure inspiratory waveforms were employed which can be expressed in equation form as follows:

Constant Pressure $$P_c(t) = P_c$$ (19)

Where:

$P_c$ is constant during inspiration and is the pressure at the carina
t=time

Increasing Pressure $$P_c(t) = mt$$ (20)

Where:

m=ramp slope
t=time
$P_c$=pressure at the carina

Rising Exponential Pressure $(\tau = T_i/n)$ (21)

$$P_c(t) = P_o e^{\frac{nt}{T_i}}$$

Rising Exponential Pressure $(\tau = T_i/5)$ (22)

$$P_c(t) = P_o e^{\frac{5t}{T_i}}$$

$t^2$ (23)

$$P_c(t) = P_o \left(\frac{t}{T_i}\right)^2$$

$$P_c(t) = P_o\left(\frac{t}{T_i}\right)^3 \tag{24}$$

Where:

$T_i$=inspiratory time $P_o$=an arbitrarily set starting point for the pressure waveform which is iteratively adjusted as the pressure waveform is maintained, and as the actually delivered tidal volume is measured, until the desired tidal volume is obtained $P_c$=pressure at the carina n=any number τ=time constant of pressure rise t=time Pressure and flowrate waveforms with time derivatives which are themselves strong functions of time, such as set forth above in equations 11–15 and 21–24, are desirable. Equations 23 and 24, for example, can be written in more general form as follows:

$$P_c(t) = P_o\left(\frac{t}{T_i}\right)^n \tag{25}$$

Where:

$T_i$=inspiratory time $P_o$=an arbitrarily set starting point for the pressure waveform which is iteratively adjusted as the pressure waveform is maintained, and as the actually delivered tidal volume is measured, until the desired tidal volume is obtained $P_c$=pressure at the carina n=any number greater than 1 t=time

A binary (normal/abnormal) approach was used in mapping out all possible combinations of $C_r$, $C_l$, $R_r$ and $R_l$. Initially, it was noted that a total of 16 different combinations of lung types are possible considering the compliances $C_r$ and $C_l$ of each lung, and flow resistances $R_r$ and $R_l$ of each respiratory pathway, as independent variables. For ease of notation, lungs with normal compliance and resistance are denoted by C and R, respectively. Abnormal lungs are denoted by C/n and mR where n and m are usually greater than 1, since clinical abnormalities normally manifest themselves as reduced compliance and increased resistance. Using these notations, the following table can be generated listing the 16 possible lung combinations:

| $R_r$ | $C_r$ | $R_l$ | $C_l$ | Lung Type |
|---|---|---|---|---|
| R | C | R | C | 1 |
| R | C | R | C/n | 2 |
| R | C | mR | C | 3 |
| R | C | mR | C/n | 5 |
| R | C/n | R | C | 2 |
| R | C/n | R | C/n | 1 |
| R | C/n | mR | C | 4 |
| R | C/n | mR | C/n | 3 |
| mR | C | R | C | 3 |
| mR | C | R | C/n | 4 |
| mR | C | mR | C | 1 |
| mR | C | mR | C/n | 2 |
| mR | C/n | R | C | 5 |
| mR | C/n | R | C/n | 3 |
| mR | C/n | mR | C | 2 |
| mR | C/n | mR | C/n | 1 |

The last line of the above column entitled "Lung type" refers to a reduced list of six lung combinations which can be distilled from the 16 possible combinations, due to functional similarities. For example, if compliances are similar but one flow resistance is twice the other, it does not matter if the higher resistance is in the right or left lung. Further, because compliance and resistance are independent of each other, the actual magnitude of the compliance compared to the resistance is not significant, and vice versa. In tabular form, the "distilled" or reduced list of possible lung configurations is given below as follows:

| Lung Type | Comparative Resistances | Comparative Compliances |
|---|---|---|
| 1 | $R_r = R_l$ | $C_r = C_l$ |
| 2 | $R_r = R_l$ | $C_r < C_l$ |
| 3 | $R_r < R_l$ | $C_r = C_l$ |
| 4 | $R_r < R_l$ | $C_r < C_l$ |
| 5 | $R_r < R_l$ | $C_r > C_l$ |
| 5a | $mR_r = R_l$ | $C_r/n = C_l$ |

The lung type labelled "5a" in the above table refers to a special configuration in which the resistance in the right lung is less than the resistance in the left lung by the same proportion as the compliance in the left lung is less than the compliance in the right lung, i.e. n=m. This category or type of lung is similar to type 1, as discussed in more detail below.

With reference to FIGS. 5–10, a computer simulation was performed for each of the lung categories or types 1–5a wherein a number of ventilatory parameters were systematically altered for comparative purposes. FIGS. 5–10 correspond to the six lung types 1–5a, respectively. With reference to the top portion of the tables of FIGS. 5–10, the categories entitled "Ventilation Parameters" include a reference to "shape," i.e. the waveform shapes utilized, inspiratory time ($T_i$), tidal volume (VT), and, inspiratory pause (IP), expressed as a percentage of the inspiratory time. Note that each of the inspiratory flowrate waveforms mentioned above, and three inspiratory pressure waveforms, were incorporated in the analysis. The abbreviations utilized to depict waveform shape in each of FIGS. 5–10, beginning at the top of the column, are as follows: constant, increasing, decreasing, half-sine (0–π), quarter-sine (π/2–π), trapezoid, decreasing exponential, shifted quarter-sine (π–3π/2) and rising exponential. The three pressure waveforms employed in the computer simulation include constant, increasing and rising exponential.

The heading "Before Pause" utilized at the top of the tables in FIGS. 5–10 refers to variables measured at the end of the active inflation period but before exhalation. The quotient $V_r/V_l$ refers to the ratio of the volume of air in each lung at the end of active inflation, which is also defined as the ventilation distribution ratio. The abbreviation MLP refers to the mean lung pressure during active inflation, expressed in centimeters of water. The variables under the heading "End of Inspiration" in FIGS. 5–10, refer to variables measured at the end of an inspiration, either with or without an inspiratory pause. $R_v(T_i)$ and MLP are the same as described above. The abbreviation PIP refers to peak inspiratory pressure, expressed in centimeters of water, which is defined as the maximum pressure within the lungs at the end of inspiration. The term $Q_{max}$ is the maximum flowrate for a given flowrate waveform and is expressed in liters per minute. The term "System τ (s)" refers to the time constant for the entire respiratory system and "iter" refers to the number of breath iterations performed in the computer simulation before a pressure waveform achieves the desired VT.

Still another method of assisting in determining the lung characteristics of a particular patient involves quantification of the effective time constant of the entire respiratory system. In the presently preferred embodiment, a constant pressure waveform (pressure step input of time duration $T_i$) is applied at the carina and an analysis is undertaken of the resulting flow rate trace at the endotracheal tube. To obtain a constant pressure waveform at the carina, the pressure is sampled at the distal tip and a feedback loop within the apparatus herein is implemented to maintain the pressure threat to the desired constant value. The flowrate at the distal tip of the endotracheal tube over time ($Q_{ett}(t)$) decays exponentially in response to a pressure step at the carina, with the maximum inspiratory flowrate, $Q_{max}$, corresponding to the initial flowrate, $Q_{ett}(t=0)$. The point in time at which $Q_{ett}(t)=\exp(-1) \cdot Q_{max}(0.368\ Q_{max})$ corresponds to the time constant of the entire respiratory system, and can be determined by measuring the flow at the endotracheal tube with the flow meter placed thereat.

Alternatively, the effective time constant of the entire respiratory system can also be quantified by an increasing ramp pressure input at the carina. For an increasing pressure waveform, $Q_{max}=Q_{ett}(T_i)$. The point in time when $Q_{ett}(t)$ reaches $(1-\exp(-1))\ Q_{max}=(1-0.368)\ Q_{max}=0.632\ Q_{max}$ is the time constant of the entire respiratory system and can be determined in the same way as with the constant pressure technique.

FIG. 11 is a condensed table of the results of the computer simulations depicted in FIGS. 5–10. The same definitions noted above are applied to the terms used in FIG. 11, and "$R_v$" is intended to refer to the ventilation distribution ratio. The results noted in FIG. 11 are expressed in narrative form with an emphasis on the qualitative trends and effects on different lung configuration types. Based upon the pattern of responses of the different lung types to different inspiratory waveforms, the original 16 different combinations of lungs can be further reduced from 6 types of lung combinations, to a total of 3 lung classes, as follows:

| Lung Class | Lung Types | Defining Conditions |
|---|---|---|
| I | 1, 5a | Equal individual time constants |
| II | 2, 4 and 5 | Unequal compliance, no restriction on resistance |
| III | 3 | Equal compliance, un-equal resistance |

Accordingly, based upon the computer modeling depicted in FIGS. 5–10 as summarized in narrative form in FIG. 11, all lung configurations can fit into three classes having distinctive differences in their dynamic response to inspiratory waveform inputs of pressure or flowrate, to an inspiratory pause (IP), and, to the time duration of inspiration ($T_i$) during mechanical ventilation. In the sections that follow, an explanation is provided as to how to clinically determine which class is correct for the lungs of a given patient, followed by a discussion of the appropriate inspiratory waveform and other ventilatory parameters for that lung class.

Clinical Determination of Lung Class

Figure 2:
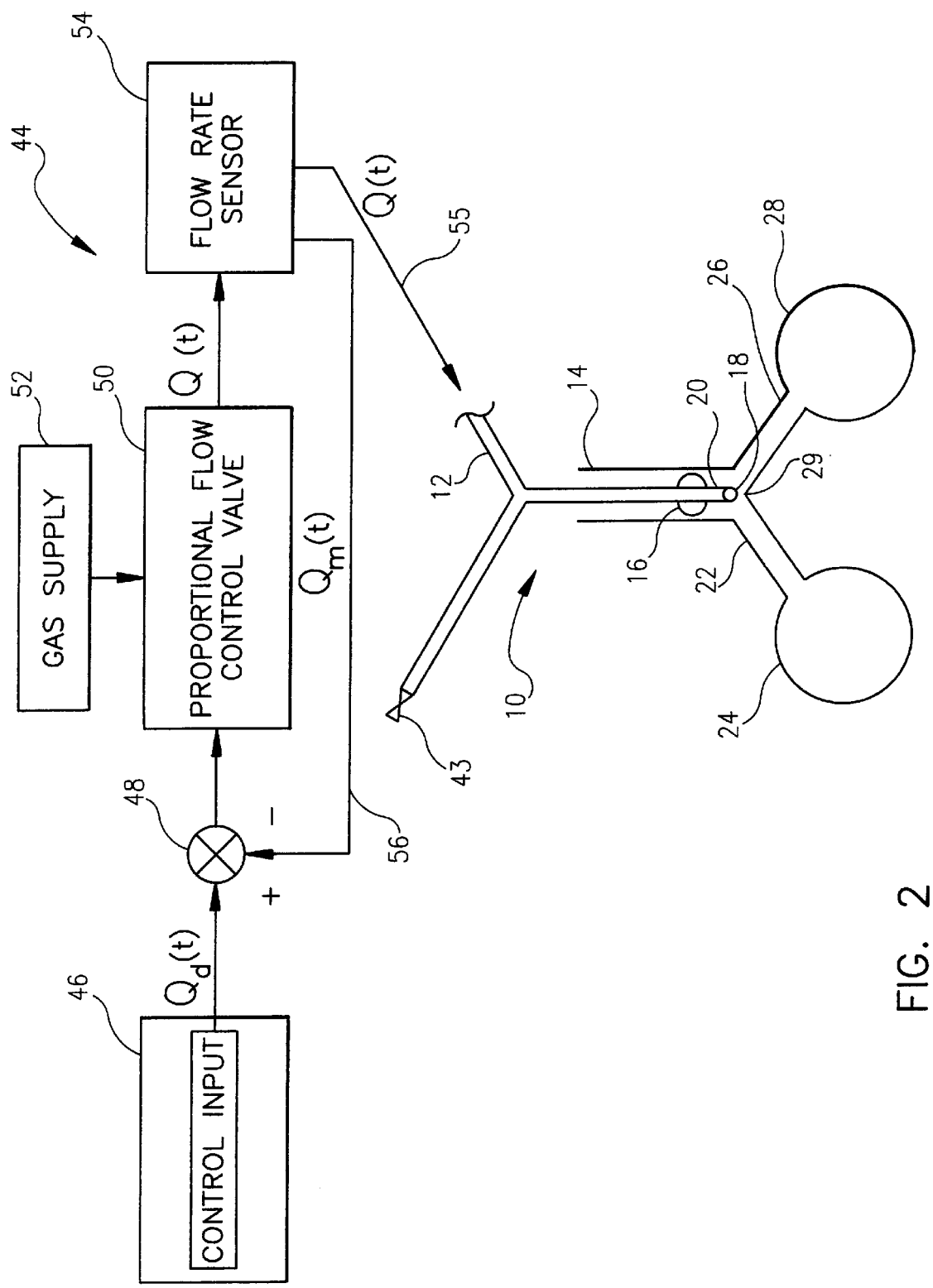
FIG. 2 is a schematic view of a closed loop ventilation system capable of obtaining flowrate waveform shaping during mechanical inspiratory.

Referring initially to FIGS. 1 and 2, two systems are depicted for introducing a particular inspiratory waveform through the Y-piece 12 and endotracheal tube 10 to the patient. The system 30 of FIG. 1 is a schematic view of an open loop configuration including a computer 32 having an internal control input, depicted graphically by the box 34, which produces an output Q(t) which is the input to a digital to analog converter represented by box 36. The digital to analog converter 36, in turn, produces a corresponding voltage V(t) which is input to what is generically referred to as "interface circuitry" at box 38. This interface circuitry 38 is representative of an element such as a voltage to current driver which is effective to convert the voltage V(t) to a corresponding current I(t), as shown in FIG. 1. The current I(t) is input to a proportional flow control valve 40 which also receives "gas" e.g. oxygen and any of anesthetics, nitrous oxide, nitric oxide, air or helium, among others, from a gas supply 42. The gas is output from the control valve 40 at a flowrate Q(t) to the Y-piece 12 connected to the endotracheal tube 10. An exhalation valve 43 is provided at the output side of the Y-piece 12. During inspiration, including the inspiratory pause, the exhalation valve 43 is closed. During exhalation, valve 43 is opened to allow the patient to exhale.

The system 44 of FIG. 2 is a diagrammatic representation of a closed loop configuration in which a control input $Q_d(t)$ from a computer depicted as box 46 is input to a comparator 48 which is connected to a proportional flow control valve 50. This flow control valve 50 receives a supply of oxygen, with or without anesthetics, nitrous oxide, nitric oxide, air, or helium, among others, from a gas supply 52. The control valve 50 discharges the gas to a flowrate sensor 54 which, in turn, inputs a gas flow Q(t) via line 55 to the Y-piece 12 connected to endotracheal tube 10. The system 44 of FIG. 2 has a feedback loop which includes the flowrate sensor 54 and line 56 connected to the comparator 48. The flowrate sensor 54 is effective to sense the actual flow of gas discharged from control valve 50 and provide a signal $Q_m(t)$ to the comparator 48 where it is compared with the input signal $Q_d(t)$ to adjust the signal input to the flow control valve 50 so that the appropriate flow rate is supplied to the patient. For purposes of illustration, the flow $Q_d(t)$ from box 46 is given a positive "+" sign and the input $Q_m(t)$ is given a "−" sign.

Although not depicted in FIG. 2, this same type of feedback loop is employed in the generation of pressure inspiratory waveforms except that pressure is sampled at the distal tip 20 of the endotracheal tube 10. This time-varying pressure sample is input to the comparator 48 where it is compared to a reference control signal in order to match the delivered pressure to the desired pressure waveform.

Either of the systems 30 or 44 depicted in FIGS. 1 and 2 can be utilized to input an inspiratory flowrate or pressure waveform of desired configuration to the endotracheal tube 10, and are effective to vary other ventilatory parameters such as inspiratory time ($T_i$), inspiratory pause (IP), and tidal volume (VT), as desired. It is contemplated that many commercially available ventilators and anesthesia machines can be utilized for this purpose, and it should be understood that the particular configuration of systems 30, 44 is given for purposes of illustration only and should in no way be considered as limiting the scope of this invention.

Before describing particular lung identification algorithms, it should be noted that certain assumptions have been made regarding operation of the systems 30 and 44. First, it is assumed that real-time end-tidal carbon dioxide values from breath to breath can be sensed through the sampling port 18 at the distal tip of the endotracheal tube 10, and supplied to the computers 32 or 46. Secondly, as described below in connection with a discussion of one algorithm wherein the pattern of ventilation is successively changed, it is assumed that a change in the ventilation pattern for two consecutive breaths does not disrupt the ventilation of the patient. Finally, it is assumed that the production of carbon dioxide within the lungs will remain constant over a duration of ten breaths (e.g. about 60 seconds) such that the end-tidal carbon dioxide detected during that ten breath period will be solely a function of the ventilation distribution ratio, i.e. the relative proportion or ratio of distribution of gas to each lung.

With reference to FIG. 11, it is observed that increased inspiratory time, $T_i$, produces an improved ventilation distribution ratio for Class III lungs while having no benefits for Class I lungs or even a worsening effect for Class II lungs. For example, from FIG. 7, using a constant flowrate waveform, it is seen that lengthening of the inspiratory time from 2.0 to 4.0 seconds, while keeping all other parameters constant, results in an improvement of the ventilation distribution ratio, $R_v(T_i)$, from 1.078 to 1.038. The control software of the computers 32 and 46 associated with systems 30 and 44 is therefore programmed to increase the inspiratory time $T_i$ while maintaining the same tidal volume and inspiratory waveform for ten consecutive breaths. In a Class III lung, it is believed that the system operator will observe a decrease in end-tidal carbon dioxide in the exhalation following ventilation with increased inspiratory time because of the better distribution of ventilation with the Class III lung. On the other hand, it is believed that an increase in inspiratory time yields no significant change in end-tidal carbon dioxide readings with a Class I lung, and can even increase the end-tidal carbon dioxide in Class II lungs. As a result, a Class III lung is positively identified with this algorithm.

Referring again to the narrative summary provided in FIG. 11, it is noted that an inspiratory pause, (IP), improves the ventilation distribution ratio for a Class III lung while having no effect on Class I lungs, and possibly a deteriorating effect on the ventilation distribution ratio for a Class II lung. With reference again to FIG. 7, it is noted that a rising exponential flowrate inspiratory waveform provides the most dramatic improvement in ventilation distribution ratio for a Class III lung using an inspiratory pause, i.e. from a level of 1.275 to 1.032. The ventilation control software of computers 32 and 46 associated with systems 30, 44 respectively, is therefore programmed to employ an exponential flowrate waveform with an inspiratory pause. For example, the patient could be ventilated with a rising exponential flowrate waveform having an inspiratory time of two seconds, without an inspiratory pause, followed by the same waveform containing a 25% inspiratory pause, e.g. 1.5 seconds active inflation, and 0.5 second pause for ten breaths or one minute. In a Class III lung, it is believed that a drop of end-tidal carbon dioxide would be sensed following ventilation with the inspiratory pause compared to the previous waveform without the inspiratory pause. It is further believed that no lowering of end-tidal carbon dioxide is seen with a Class I lung, and Class II lungs will produce either no change or an increase in end-tidal carbon dioxide.

Another algorithm can be utilized for lung classification in which inspiratory waveforms are changed between consecutive breaths, and the following discussion is based on a belief of the clinical results of the use of same. For example, the narrative table in FIG. 11 indicates that if a constant pressure waveform is immediately followed by ventilation for ten breaths or one minute with a rising exponential flowrate waveform of the same tidal volume and the same inspiratory time, a rise in end-tidal carbon dioxide follows ventilation with the rising exponential flowrate waveform for a Class III lung. No change in end-tidal carbon dioxide is produced with a Class I lung, under these ventilation conditions, and Class II lungs produce a decrease in end-tidal carbon dioxide. The computers 32 and 46 associated with systems 30, 44 respectively, are therefore programmed to first introduce a constant pressure waveform and then a rising exponential flowrate waveform with the tidal volume and inspiratory time being maintained constant. When using system 44, it is recommended that the constant pressure waveform be preceded by several constant pressure breaths so that the feedback loop can be set to produce the desired tidal volume before end-tidal carbon dioxide is measured.

The foregoing discussion has been primarily directed to lung classification algorithms intended to distinguish Class III lungs from Class I and II lungs. As discussed below, although patients having Class I or II lungs can be appropriately ventilated with many of the same inspiratory waveforms, in some instances it may be desirable to distinguish the patients with Class I and II lungs. For this purpose, it is noted that the computer simulation performed to generate the data in FIGS. 5–10 was predicated upon the assumption that the pressure in each lung of Class I lungs is substantially equal during the entire inflation period. As such, if an inspiratory flowrate waveform is followed by an inspiratory pause, it is believed there will be no gas redistribution or "pendelluft" in patients with Class I lungs. The term pendelluft refers to a redistribution of gas from one lung to the other in the event the pressure within one lung is greater than the other. If this occurs, the gas within the higher pressure lung will flow to the lung of lower pressure so that the pressure between the two lungs is substantially equalized. In the absence of pendelluft, the pressure at the carina, as sensed at the sampling port 18 at the distal tip of the endotracheal tube 10, drops sharply during an inspiratory pause to a flat plateau.

It is further believed that in a Class III lung, on the other hand, where pressures are not generally equal in each lung at the end of active inflation, there is gas redistribution during the inspiratory pause according to the pressure differential between the lungs. Such redistribution of gas flow during the inspiratory pause causes the pressure at the carina to decay in an exponential fashion to a plateau rather than falling steeply to a plateau as in Class I lungs. Such gas redistribution and exponential decay in pressure at the carina therefore provides a means of differentiation between Class I and Class III lungs.

Selection Of And Ventilation With An Appropriate Flowrate Waveform

The purpose of selecting an appropriate inspiratory waveform in lungs of unequal time constant, i.e. different compliances and/or resistances, is to match the ventilation or gas flowrate to the perfusion or blood flowrate. As discussed above, the presence of different gas volumes in the right and left lung can create an undesirable ventilation/perfusion ratio mismatch which degrades the rate of gas exchange, and the efficiency of gas exchange, at the blood/gas interface within the lungs. While the body's compensatory mechanisms shunt the blood flow to favor the better ventilated lung, there is a limit to that self-regulatory action which can be depressed by some anesthetics. The objective, therefore, is to obtain a ventilation distribution ratio which is as close to unity as possible, e.g.:

$$R_v(T_i) = V_r(T_i)/V_l(T_i)$$
$$= 1$$

In addition to obtaining a ventilation distribution ratio as close to 1 as possible, inspiratory waveforms must be chosen to minimize the mean lung pressure or time-averaged pressure experienced by the lungs during an inspiratory cycle. As discussed above, higher mean lung pressures during mechanical ventilation can reduce the cardiac output by interfering with the filling and emptying of the heart since the lungs and heart both reside within the chest cavity. With these factors in mind, appropriate ventilation conditions for each lung can be summarized as follows.

Class I Lungs

Class I lungs have been defined above as having equal time constants for both respiratory pathways. That is, the product of the resistance and compliance (RC) is equal for both the right and left respiratory pathways. In Class I lungs, the ventilation distribution ratio is independent of the shape of the inspiratory waveform, independent of the duration of inspiration, $T_i$, and is not affected by the presence or duration of an inspiratory pause, IP. The ventilation distribution ratio is determined by the compliance ratio ($C_r/C_l$,) only. While it is contemplated that a number of inspiratory waveforms would be suitable for use with Class I lungs, it is noted that the increasing exponential waveform produces the lowest mean lung pressure over time in Class I lungs, which makes its use potentially the most desirable. It is also noted that an inspiratory pause increases the mean lung pressure within Class I lungs, and is therefore not recommended.

Class II Lungs

A number of recommendations regarding waveform shape, inspiratory time and inspiratory pause can also be made for Class II lungs (unequal compliance, equal or unequal resistance) based upon the data compiled in FIGS. 5–11. As with Class I lungs, the rising exponential waveform produces the lowest mean pressure within Class II lungs and is probably the best choice, although other waveforms are useful. Regardless of the shape of the inspiratory waveform, a shorter inspiratory time tends to produce a more even ventilation distribution ratio and is recommended for Class II lungs. An inspiratory pause worsens the ventilation distribution ratio and increases the mean lung pressure within Class II lungs, and is therefore not recommended.

Class III Lungs

With respect to Class III lungs (equal compliance, unequal resistance), a selection of different waveforms is probably best made in a clinical setting with the following guidelines. It has been found that a rising exponential flowrate waveform produces the lowest mean lung pressure within patients having Class III lungs, but the resulting ventilation distribution ratio is most uneven. A constant pressure waveform, on the other hand, produces the highest level of mean lung pressure for Class III lungs but also results in the most even ventilation distribution ratio. The selection of one or the other of these waveforms will therefore depend on the clinician's evaluation of the condition of a particular patient.

It is also apparent from the data in FIGS. 5–10 that an inspiratory pause, regardless of the type of waveform, improves the ventilation distribution ratio and is strongly recommended for Class III lungs. Further, increased inspiratory time also evens the ventilation distribution ratio and produces a lower mean lung pressure in Class III lungs. Accordingly, a constant pressure or a decaying exponential flowrate waveform with a longer inspiratory time, and an inspiratory pause, produce good ventilation distribution in Class III lungs.

The methodology of this invention therefore involves a clinical determination or identification of the class of the lungs of a particular patient, followed by the selection of an appropriate inspiratory waveform, inspiratory pause (if any) and inspiratory time to produce a ventilation distribution ratio as close to unity as possible while minimizing the mean lung pressure. This methodology improves the mass transfer rate and efficiency at the blood/gas interface within the lungs to achieve better delivery of oxygen and anesthetics into the blood stream and removal of carbon dioxide and anesthetics therefrom during artificial ventilation.

While the invention has been described with reference to a preferred embodiment, it will be understood by those skilled in the art that various changes may be made and equivalence may be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of artificially ventilating a patient, comprising:

determining the class of lungs of the patient, the determining of the class of lungs comprising determining whether the patient has lungs with equal individual time constants, lungs of unequal compliance with no restriction on resistance, or lungs with equal compliance and unequal resistance;

selecting an appropriate inspiratory waveform for the particular lung class of such patient; and ventilating such patient with the selected inspiratory waveform.

2. A method of artificially ventilating a patient, comprising:

determining the class of lungs of the patient, the determining of the class of lungs comprising ventilating the patient with an inspiratory waveform having a first inspiratory time, thereafter ventilating the patient with said inspiratory waveform for a second inspiratory time which is greater than said first inspiratory time throughout a selected period or number of breaths while maintaining tidal volume constant, sensing the end-tidal carbon dioxide concentration of the gas exhaled by the patient following each of said inspiratory waveforms, and comparing said sensed concentration of end-title carbon dioxide;

selecting an appropriate inspiratory waveform for the particular lung class of such patient; and ventilating such patient with the selected inspiratory waveform.

3. The method of claim 2 in which said step of thereafter ventilating the patient includes thereafter ventilating the patient with said inspiratory waveform for a second inspiratory time which is greater than said first inspiratory time for at least ten breaths or about one minute while maintaining tidal volume constant.

4. A method of artificially ventilating a patient, comprising:

determining the class of lungs of the patient, the determining of the class of lungs comprising ventilating the patient with an inspiratory waveform without inspiratory pause, thereafter ventilating the patient with said inspiratory waveform containing an inspiratory pause while maintaining tidal volume constant for a selected period, sensing the end-tidal carbon dioxide concentration of the gas exhaled by the patient following each of said inspiratory waveforms, and comparing said sensed concentration of end-title carbon dioxide;

selecting an appropriate inspiratory waveform for the particular lung class of such patient; and ventilating such patient with the selected inspiratory waveform.

5. The method of claim 4 in which said steps of ventilating the patient comprises ventilating the patient with a rising exponential flowrate inspiratory waveform.

6. A method of artificially ventilating a patient, comprising:

determining the class of lungs of the patient, the determining of the class of lungs comprising ventilating the patient with a constant pressure inspiratory waveform having a selected tidal volume and inspiratory time, thereafter ventilating the patient with a rising exponential flowrate waveform having the same tidal volume and inspiratory time as said constant pressure waveform for a selected time period, sensing the end-tidal carbon dioxide concentration of the gas exhaled by the patient following each of said inspiratory waveforms, and comparing said sensed concentration of end-title carbon dioxide;

selecting an appropriate inspiratory waveform for the particular lung class of such patient; and ventilating such patient with the selected inspiratory waveform.

7. A method of artificially ventilating a patient, comprising:

determining the class of lungs of the patient;

selecting an appropriate inspiratory waveform for the particular lung class of such patient, the selecting of the appropriate inspiratory waveform comprising selecting a quarter-sine ($\pi/2 - \pi$) flowrate waveform defined as follows:

$$Q_{ett}(t) = \frac{\pi VT}{2T_i} \sin\left(\frac{\pi}{2} + \frac{\pi}{2T_i} \cdot t\right)$$

where:

$Q_{ett}(t)$=total flowrate at the trachea or endotracheal tube, over time

VT=tidal volume $T_i$=inspiratory volume t=time; and ventilating such patient with the selected inspiratory waveform.

8. A method of artificially ventilating a patient, comprising:

determining the class of lungs of the patient;

selecting an appropriate inspiratory waveform for the particular lung class of such patient, the selecting of an appropriate inspiratory waveform comprising selecting a quarter-sine ($\pi - 3\pi/2$) flowrate waveform defined as follows:

$$Q_{ett}(t) = \frac{VT}{T_i \cdot \left(1 - \frac{2}{\pi}\right)} \left(1 + \sin\left(\pi + \frac{\pi}{2T_i}t\right)\right)$$

where:

$Q_{ett}(t)$=total flowrate at the trachea or endotracheal tube, over time

VT=tidal volume $T_i$=inspiratory volume t=time; and ventilating such patient with the selected inspiratory waveform.

9. A method of artificially ventilating a patient, comprising:

determining the class of lungs of the patient;

selecting an appropriate inspiratory waveform for the particular lung class of such patient, the selecting of an appropriate inspiratory waveform comprising selecting a trapezoid flowrate waveform defined as follows:

$$Q_{ett}\left(0 \le t < \frac{T_i}{2}\right) = \frac{4VT}{3Ti}$$

$$Q_{ett}\left(\frac{T_i}{2} \le t \le T_i\right) = -\frac{8VT}{3T_i^2} \cdot \left(t - \frac{T_i}{2}\right) + \frac{4VT}{3T_i}$$

where:

$Q_{ett}(t)$=total flowrate at the trachea or endotracheal tube, over time

VT=tidal volume $T_i$=inspiratory volume t=time; and ventilating such patient with the selected inspiratory waveform.

10. A method of artificially ventilating a patient, comprising:

determining the class of lungs of the patient;

selecting an appropriate inspiratory waveform for the particular lung class of such patient, the selecting of an appropriate inspiratory waveform comprising selecting a decaying exponential ($\tau = T_i/n$) flowrate waveform defined as follows:

$$Q_{ett}(t) = f[VT, T_i]e^{\frac{-nt}{T_i}}$$

where:

$Q_{ett}(t)$=total flowrate at the trachea or endotracheal tube, over time

VT=tidal volume $T_i$=inspiratory volume

τ=time constant of flowrate decay n=any number t=time; and ventilating such patient with the selected inspiratory waveform.

11. A method of artificially ventilating a patient, comprising:

determining the class of lungs of the patient;

selecting an appropriate inspiratory waveform for the particular lung class of such patient, the selecting of an appropriate inspiratory waveform comprising selecting a decaying exponential ($\tau=T_i/5$) flowrate waveform defined as follows:

$$Q_{ett}(t) = \frac{VT}{0.198652 T_i} e^{\frac{-5t}{T_i}}$$

where:
$Q_{ett}(t)$=total flowrate at the trachea or endotracheal tube, over time
VT=tidal volume
$T_i$=inspiratory volume
$\tau$=time constant of flowrate decay
t=time; and
ventilating such patient with the selected inspiratory waveform.

12. A method of artificially ventilating a patient, comprising:
determining the class of lungs of the patient;
selecting an appropriate inspiratory waveform for the particular lung class of such patient, the selecting of an appropriate inspiratory waveform comprising selecting a rising exponential ($\tau=T_i/n$) flowrate waveform defined as follows:

$$Q_{ett}(t) = f[VT, T_i] e^{\frac{nt}{T_i}}$$

where:
$Q_{ett}(t)$=total flowrate at the trachea or endotracheal tube, over time
VT=tidal volume
$T_i$=inspiratory volume
$\tau$=time constant of flowrate decay
n=any number
t=time; and
ventilating such patient with the selected inspiratory waveform.

13. A method of artificially ventilating a patient, comprising:
determining the class of lungs of the patient;
selecting an appropriate inspiratory waveform for the particular lung class of such patient, the selecting of an appropriate inspiratory waveform comprising selecting a rising exponential ($\tau=T_i/5$) flowrate waveform defined as follows:

$$Q_{ett}(t) = \frac{0.033918 VT}{T_i} e^{\frac{5t}{T_i}}$$

where:
$Q_{ett}(t)$=total flowrate at the trachea or endotracheal tube, over time
VT=tidal volume
$T_i$=inspiratory volume
$\tau$=time constant of flowrate decay
t=time; and
ventilating such patient with the selected inspiratory waveform.

14. A method of artificially ventilating a patient, comprising:
determining the class of lungs of the patient;
selecting an appropriate inspiratory waveform for the particular lung class of such patient, the selecting of an appropriate inspiratory waveform comprising selecting a flowrate waveform defined as follows:

$$Q_{ett}(t) = \frac{3 VT \cdot t^2}{T_i^3}$$

where:
$Q_{ett}(t)$=total flowrate at the trachea or endotracheal tube, over time
VT=tidal volume
$T_i$=inspiratory volume
t=time; and
ventilating such patient with the selected inspiratory waveform.

15. A method of artificially ventilating a patient, comprising:
determining the class of lungs of the patient;
selecting an appropriate inspiratory waveform for the particular lung class of such patient, the selecting of an appropriate inspiratory waveform comprising selecting a flowrate waveform defined as follows:

$$Q_{ett}(t) = \frac{4 VT \cdot t^3}{T_i^4}$$

where:
$Q_{ett}(t)$=total flowrate at the trachea or endotracheal tube, over time
VT=tidal volume
$T_i$=inspiratory volume
t=time; and
ventilating such patient with the selected inspiratory waveform.

16. A method of artificially ventilating a patient, comprising:
determining the class of lungs of the patient;
selecting an appropriate inspiratory waveform for the particular lung class of such patient, the selecting of an appropriate inspiratory waveform comprising selecting a flowrate waveform defined as follows:

$$Q_{ett}(t) = \frac{(n+1) VT}{T_i^{n+1}} \cdot t^n$$

where:
$Q_{ett}(t)$=total flowrate at the trachea or endotracheal tube, over time
VT=tidal volume
$T_i$=inspiratory volume
t=time
n=any number; and
ventilating such patient with the selected inspiratory waveform.

17. A method of artificially ventilating a patient, comprising:
determining the class of lungs of the patient;
selecting an appropriate inspiratory waveform for the particular lung class of such patient, the selecting of an appropriate inspiratory waveform comprising selecting a flowrate waveform defined as follows:

$$Q_{ett}(t) = A e^{at}$$

where:

$$A = \frac{\alpha}{e^{\alpha T_i} - 1} VT$$

$$\alpha = \frac{|C_l - C_r|}{C_l C_r |(R_l - R_r)|}$$

$C_r$=right lung compliance
$C_l$=left lung compliance
$R_r$=right lung resistance
$R_l$=left lung resistance
VT=tidal volume
$Q_{ett}(t)$=total flowrate at the trachea or endotracheal tube, over time
$T_i$=inspiratory volume
t=time; and ventilating such patient with the selected inspiratory waveform.

18. A method of artificially ventilating a patient, comprising:

determining the class of lungs of the patient;

selecting an appropriate inspiratory waveform for the particular lung class of such patient, the selecting of an appropriate inspiratory waveform comprising selecting a constant pressure waveform defined as follows:

$$P_c(t) = P_c$$

where:
$P_c$ is constant during inspiration and is the pressure at the carina which is iteratively adjusted while the constant pressure waveform is maintained until the desired tidal column is obtained
t=time; and ventilating such patient with the selected inspiratory waveform.

19. A method of artificially ventilating a patient, comprising:

determining the class of lungs of the patient;

selecting an appropriate inspiratory waveform for the particular lung class of such patient, the selecting of an appropriate inspiratory waveform comprising selecting a rising exponential pressure waveform defined as follows:

$$P_c(t) = P_o e^{\frac{nt}{T_i}}$$

where:
$T_i$=inspiratory time
$P_o$=an arbitrarily set starting point for the pressure waveform which is iteratively adjusted as the pressure waveform is maintained, and as the actually delivered tidal volume is measured, until the desired tidal volume is obtained
$P_c$=pressure at carina
n=any number
t=time; and ventilating such patient with the selected inspiratory waveform.

20. A method of artificially ventilating a patient, comprising:

determining the class of lungs of the patient;

selecting an appropriate inspiratory waveform for the particular lung class of such patient, the selecting of an appropriate inspiratory waveform comprising selecting a pressure waveform, $t^2$, defined as follows:

$$P_c(t) = P_o \left(\frac{t}{T_i}\right)^2$$

where:
$T_i$=inspiratory time
$P_o$=an arbitrarily set starting point for the pressure waveform which is iteratively adjusted as the pressure waveform is maintained, and as the actually delivered tidal volume is measured, until the desired tidal volume is obtained
$P_c$=pressure at carina
t=time; and ventilating such patient with the selected inspiratory waveform.

21. A method of artificially ventilating a patient, comprising:

determining the class of lungs of the patient;

selecting an appropriate inspiratory waveform for the particular lung class of such patient, the selecting of an appropriate inspiratory waveform comprising selecting a pressure waveform, $t^3$, defined as follows:

$$P_c(t) = P_o \left(\frac{t}{T_i}\right)^3$$

where:
$T_i$=inspiratory time
$P_o$=an arbitrarily set starting point for the pressure waveform which is iteratively adjusted as the pressure waveform is maintained, and as the actually delivered tidal volume is measured, until the desired tidal volume is obtained
$P_c$=pressure at carina
t=time; and ventilating such patient with the selected inspiratory waveform.

22. A method of artificially ventilating a patient, comprising:

determining the class of lungs of the patient;

selecting an appropriate inspiratory waveform for the particular lung class of such patient, the selecting of an appropriate inspiratory waveform comprising selecting a pressure waveform, $t^n$, defined as follows:

$$P_c(t) = P_o \left(\frac{t}{T_i}\right)^n$$

where:
$T_i$=inspiratory time
$P_o$=an arbitrarily set starting point for the pressure waveform which is iteratively adjusted as the pressure waveform is maintained, and as the actually delivered tidal volume is measured, until the desired tidal volume is obtained
$P_c$=pressure at carina
n=any number greater than 1
t=time; and ventilating such patient with the selected inspiratory waveform.

23. A method of artificially ventilating a patient, comprising:

determining the class of lungs of the patient, the determining the class of lungs comprising determining whether the patient has lungs with equal individual time constraints, lungs of unequal compliance with no restriction on resistance, or lungs with equal compliance and unequal resistance;

selecting an inspiratory waveform having an appropriate shape inspiratory time and inspiratory pause for the lung class of such patient; and ventilating such patient with the selected inspiratory waveform.

24. A method of artificially ventilating a patient, comprising:

determining the class of lungs of the patient;

selecting an inspiratory waveform having an appropriate shape inspiratory time and inspiratory pause for the lung class of such patient, the selecting of an appropriate appropriate inspiratory waveform comprising selecting an inspiratory waveform with zero inspiratory pause for lungs with equal individual time constraints; and ventilating such patient with the selected inspiratory waveform.

25. A method of artificially ventilating a patient, comprising:

determining the class of lungs of the patient;

selecting an inspiratory waveform having an appropriate shape inspiratory time and inspiratory pause for the lung class of such patient, the selecting of an appropriate appropriate inspiratory waveform comprising selecting an inspiratory waveform with a comparatively short inspiratory time for lungs of unequal compliance with no restriction on resistance; and ventilating such patient with the selected inspiratory waveform.

26. A method of artificially ventilating a patient, comprising:

determining the class of lungs of the patient;

selecting an inspiratory waveform having an appropriate shape inspiratory time and inspiratory pause for the lung class of such patient, the selecting of an appropriate inspiratory waveform comprising selecting an inspiratory waveform with zero inspiratory pause for lungs of unequal compliance with no restriction on resistance; and ventilating such patient with the selected inspiratory waveform.

27. A method of artificially ventilating a patient, comprising:

determining the class of lungs of the patient;

selecting an inspiratory waveform having an appropriate shape inspiratory time and inspiratory pause for the lung class of such patient, the selecting of an appropriate inspiratory waveform comprising selecting an inspiratory waveform having an inspiratory pause on the order of about 25% of the inspiratory time for lungs with equal compliance with unequal resistance; and ventilating such patient with the selected inspiratory waveform.

28. A method of artificially ventilating a patient, comprising:

determining the class of lungs of the patient;

selecting an inspiratory waveform having an appropriate shape inspiratory time and inspiratory pause for the lung class of such patient, the selecting of an appropriate inspiratory waveform comprising selecting an inspiratory waveform with a comparatively long inspiratory time for lungs of equal compliance with unequal resistance; and ventilating such patient with the selected inspiratory waveform.

29. A method of artificially ventilating a patient, comprising:

determining the class of lungs of the patient;

selecting an inspiratory waveform having an appropriate shape inspiratory time and inspiratory pause for the lung class of such patient, the selecting of an appropriate inspiratory waveform comprising selecting at least one of the flowrate waveforms defined as follows:

Quarter sine $(\pi/2 - \pi)$ $$Q_{ett}(t) = \frac{\pi VT}{2T_i} \sin\left(\frac{\pi}{2} + \frac{\pi}{2T_i} \cdot t\right)$$

Shifted Quarter Sine $(\pi - 3\pi/2)$ $$Q_{ett}(t) = \frac{VT}{T_i \cdot \left(1 - \frac{2}{\pi}\right)} \left(1 + \sin\left(\pi + \frac{\pi}{2T_i} t\right)\right)$$

Trapezoid $$Q_{ett}\left(0 \leq t < \frac{T_i}{2}\right) = \frac{4VT}{3T_i}$$

$$Q_{ett}\left(\frac{T_i}{2} \leq t \leq T_i\right) = -\frac{8VT}{3T_i^2} \cdot \left(t - \frac{T_i}{2}\right) + \frac{4VT}{3T_i}$$

Decaying Exponential $(\tau = T_i/n)$ $$Q_{ett}(t) = f[VT, T_i] e^{\frac{-nt}{T_i}}$$

Decaying Exponential $(\tau = T_i/5)$ $$Q_{ett}(t) = \frac{VT}{0.198652 T_i} e^{\frac{-5t}{T_i}}$$

Rising Exponential $(\tau = T_i/n)$ $$Q_{ett}(t) = f[VT, T_i] e^{\frac{nt}{T_i}}$$

Rising Exponential $(\tau = T_i/5)$ $$Q_{ett}(t) = \frac{0.033918 VT}{T_i} e^{\frac{5t}{T_i}}$$

Ideal Increasing Exponential $$Q_{ett}(t) = A e^{\alpha t}$$

$t^2$ $$Q_{ett}(t) = \frac{3VT \cdot t^2}{T_i^3}$$

$t^3$

-continued $$Q_{ett}(t) = \frac{4VT \cdot t^3}{T_i^4}$$

$t^n$ $$Q_{ett}(t) = \frac{(n+1)VT}{T_i^{n+1}} \cdot t^n$$

Where:

$$A = \frac{\alpha}{e^{\alpha T_i} - 1} VT$$

$$\alpha = \frac{|C_l - C_r|}{C_l C_r |(R_l - R_r)|}$$

$Q_{ett}(t)$=total flowrate at the trachea or endotracheal tube, over time
VT=tidal volume
$T_i$=inspiratory volume
τ=time constant of flowrate decay
n=any number
f[VT, $T_i$]=a constant which is a fraction of VT and $T_i$
T=time
$C_r$=right lung compliance
$C_l$=left lung compliance
$R_r$=right lung resistance
$R_l$=left lung resistance; and
ventilating such patient with the selected inspiratory waveform.

30. A method of artificially ventilating a patient, comprising:
determining the class of lungs of the patient;
selecting an inspiratory waveform having an appropriate shape, inspiratory time and inspiratory pause for the lung class of such patient, the selecting of the inspiratory waveform comprising selecting an inspiratory time based at least in part on the effective time constant of the entire respiratory system comprising applying a constant pressure waveform at the carina of the patient through an endotracheal tube with which the patient is intubated and determining the point at which the flowrate at the endotracheal tube, $Q_{ett}(t)$, is equal to exp $(-1) \cdot Q_{max}(0.368\ Q_{max})$, where $Q_{max}$ is the maximum inspiratory flowrate, which point is the effective time constant of the entire respiratory system; and
ventilating such patient with the selected inspiratory waveform.

31. A method of artificially ventilating a patient, comprising:
determining the class of lungs of the patient;
selecting an inspiratory waveform having an appropriate shape inspiratory time and inspiratory pause for the lung class of such patient, the selecting of the inspiratory waveform comprising selecting an inspiratory time based at least in part on the effective time constant of the entire respiratory system comprising applying an increasing ramp pressure waveform at the carina of the patient through an endotracheal tube with which the patient is intubated and determining the point at which the flowrate at the endotracheal tube, $Q_{ett}(t)$, is equal to $(1-\exp(-1))\ Q_{max}=(1-0.368)Q_{max}=0.632\ Q_{max}$, where $Q_{max}$ is equal to $Q_{ett}(T_i)$ and $T_i$ is the inspiratory time, which point is the effective time constant of the entire respiratory system; and
ventilating such patient with the selected inspiratory waveform.

* * * * *